(12) United States Patent
Thenuwara et al.

(10) Patent No.: US 8,954,143 B2
(45) Date of Patent: Feb. 10, 2015

(54) RADIAL FEED THROUGH PACKAGING FOR AN IMPLANTABLE ELECTROACUPUNCTURE DEVICE

(71) Applicant: Valencia Technologies Corporation, Valencia, CA (US)

(72) Inventors: Chuladatta H. Thenuwara, Castaic, CA (US); David K. L. Peterson, Valencia, CA (US)

(73) Assignee: Valencia Technologies Corporation, Valencia, CA (US)

( * ) Notice: Subject to any disclaimer, the term of this patent is extended or adjusted under 35 U.S.C. 154(b) by 18 days.

(21) Appl. No.: 13/777,901

(22) Filed: Feb. 26, 2013

(65) Prior Publication Data

US 2014/0214133 A1    Jul. 31, 2014

Related U.S. Application Data

(63) Continuation-in-part of application No. 13/598,582, filed on Aug. 29, 2012.

(60) Provisional application No. 61/606,995, filed on Mar. 6, 2012, provisional application No. 61/676,275, filed on Jul. 26, 2012.

(51) Int. Cl.
*A61N 1/18* (2006.01)
*A61N 1/375* (2006.01)

(52) U.S. Cl.
CPC .................................... *A61N 1/375* (2013.01)
USPC ............................................................ 607/2

(58) Field of Classification Search
USPC ...................................... 607/2, 3, 35, 44–46
See application file for complete search history.

(56) References Cited

U.S. PATENT DOCUMENTS 4,031,899 A    6/1977  Renirie
4,157,720 A *  6/1979  Greatbatch ..................... 607/36

(Continued)

FOREIGN PATENT DOCUMENTS

WO       WO 02/00294 A1    1/2002

OTHER PUBLICATIONS

WHO Standard Acupuncture Point Locations in the Western Pacific Region, World Health Organization (WHO), Western Pacific Region, 2008 (updated and reprinted 2009), ISBN 978 92 9061 248 7. The Table of Contents, Forward (v-vi), General Guidelines for Acupuncture Point Locations (1-21) as well as pp. 33, 35, 39, 45, 64, 151, 154, 171, 188, and 197.

(Continued)

*Primary Examiner* — Rex R Holmes
(74) *Attorney, Agent, or Firm* — Bryant R. Gold

(57) ABSTRACT

An implantable electroacupuncture device (IEAD) treats a disease or medical condition of a patient through application of stimulation pulses applied at a specified acupoint or other target tissue location. In a preferred implementation, the IEAD is an implantable, coin-sized, self-contained, leadless electroacupuncture device having at least two electrodes attached to an outside surface of its housing. The device generates stimulation pulses in accordance with a specified stimulation regimen. Power management circuitry within the device allows a primary battery, having a high internal impedance, to be used to power the device. The stimulation regimen generates stimulation pulses during a stimulation session of duration T3 minutes applied every T4 minutes. The duty cycle, or ratio T3/T4, is very low, no greater than 0.05. The low duty cycle and careful power management allow the IEAD to perform its intended function for several years.

5 Claims, 15 Drawing Sheets

(56) References Cited

U.S. PATENT DOCUMENTS

| | | | |
|---|---|---|---|
| 4,345,604 A | 8/1982 | Renirie | |
| 4,528,072 A | 7/1985 | Kurosawa | |
| 4,535,784 A | 8/1985 | Rohlicek | |
| 4,566,064 A | 1/1986 | Whitaker | |
| 5,195,517 A | 3/1993 | Chen | |
| 5,199,428 A | 4/1993 | Obel | |
| 5,211,175 A | 5/1993 | Gleason | |
| 5,250,068 A | 10/1993 | Ideguchi | |
| 5,251,637 A | 10/1993 | Shalvi | |
| 5,372,605 A | 12/1994 | Adams | |
| 5,544,656 A | 8/1996 | Pitsillides | |
| 5,707,400 A | 1/1998 | Terry, Jr. | |
| 5,891,181 A | 4/1999 | Zhu | |
| 6,006,134 A | 12/1999 | Hill | |
| 6,178,352 B1 | 1/2001 | Gruzdowich | |
| 6,393,324 B2 | 5/2002 | Gruzdowich | |
| 6,522,926 B1 | 2/2003 | Kieval | |
| 6,658,298 B2 | 12/2003 | Gruzdowich | |
| 6,735,475 B1 | 5/2004 | Whitehurst | |
| 6,839,596 B2 | 1/2005 | Nelson | |
| 6,950,707 B2 | 9/2005 | Whitehurst | |
| 6,978,174 B2 | 12/2005 | Gelfand | |
| 7,003,352 B1 | 2/2006 | Whitehurst | |
| 7,013,177 B1 | 3/2006 | Whitehurst | |
| 7,046,499 B1 * | 5/2006 | Imani et al. | 361/302 |
| 7,136,701 B2 | 11/2006 | Greatbatch | |
| 7,155,279 B2 | 12/2006 | Whitehurst | |
| 7,162,303 B2 | 1/2007 | Levin | |
| 7,171,266 B2 | 1/2007 | Gruzdowich | |
| 7,203,548 B2 | 4/2007 | Whitehurst | |
| 7,292,890 B2 | 11/2007 | Whitehurst | |
| 7,321,792 B1 | 1/2008 | Min et al. | |
| 7,373,204 B2 | 5/2008 | Gelfand | |
| 7,440,806 B1 | 10/2008 | Whitehurst | |
| 7,610,100 B2 | 10/2009 | Jaax | |
| 7,620,451 B2 | 11/2009 | Demarais | |
| 7,657,316 B2 | 2/2010 | Jaax | |
| 7,962,219 B2 | 6/2011 | Jaax | |
| 2003/0078642 A1 | 4/2003 | Malaney | |
| 2003/0158588 A1 | 8/2003 | Rizzo | |
| 2003/0187485 A1 | 10/2003 | Sturman | |
| 2003/0195583 A1 | 10/2003 | Gruzdowich | |
| 2003/0195585 A1 | 10/2003 | Gruzdowich | |
| 2005/0107832 A1 | 5/2005 | Bernabei | |
| 2005/0228460 A1 | 10/2005 | Levin | |
| 2005/0234533 A1 | 10/2005 | Schulman | |
| 2006/0041283 A1 | 2/2006 | Gelfand | |
| 2007/0005119 A1 | 1/2007 | Crohn | |
| 2007/0219595 A1 | 9/2007 | He | |
| 2007/0255319 A1 | 11/2007 | Greenberg | |
| 2007/0265680 A1 | 11/2007 | Liu | |
| 2008/0091255 A1 | 4/2008 | Caparso | |
| 2009/0192555 A1 | 7/2009 | Schleicher | |
| 2009/0210026 A1 | 8/2009 | Solberg | |
| 2009/0292341 A1 | 11/2009 | Parramon | |
| 2010/0069992 A1 | 3/2010 | Aghassian | |
| 2010/0211132 A1 | 8/2010 | Nimmagadda | |
| 2010/0324624 A1 | 12/2010 | Chang | |
| 2010/0327887 A1 | 12/2010 | Denison | |
| 2011/0106220 A1 | 5/2011 | DeGiorgio | |
| 2011/0112603 A1 | 5/2011 | DeGiorgio | |
| 2011/0172739 A1 | 7/2011 | Mann | |
| 2011/0218589 A1 | 9/2011 | DeGiorgio | |
| 2011/0218590 A1 | 9/2011 | DeGiorgio | |
| 2012/0022612 A1 | 1/2012 | Littlewood | |
| 2012/0259390 A1 | 10/2012 | Canion | |
| 2013/0041396 A1 | 2/2013 | Ryotokuji | |
| 2014/0214111 A1 | 7/2014 | Greiner | |
| 2014/0214112 A1 | 7/2014 | Greiner | |
| 2014/0214113 A1 | 7/2014 | Greiner | |
| 2014/0214114 A1 | 7/2014 | Greiner | |
| 2014/0214115 A1 | 7/2014 | Greiner | |
| 2014/0214116 A1 | 7/2014 | Peterson | |
| 2014/0214117 A1 | 7/2014 | Greiner | |
| 2014/0214118 A1 | 7/2014 | Greiner | |
| 2014/0214119 A1 | 7/2014 | Greiner | |
| 2014/0214124 A1 | 7/2014 | Greiner | |
| 2014/0214125 A1 | 7/2014 | Greiner | |
| 2014/0214126 A1 | 7/2014 | Greiner | |
| 2014/0214127 A1 | 7/2014 | Greiner | |
| 2014/0214128 A1 | 7/2014 | Peterson | |
| 2014/0214134 A1 | 7/2014 | Peterson | |
| 2014/0214144 A1 | 7/2014 | Peterson | |

OTHER PUBLICATIONS

"Electroacupuncture." http://en.wikipedia.org/wiki/Electroacupuncture.

"Acupuncture Today: Electroacupuncture". Feb. 1, 2001 (retrieved on-line Aug. 9, 2006 at http://www.acupuncturetoday.com/abc/electroacupuncture.php).

Li. "Neural Mechanism of Electroacupuncture's Hypotensive Effects", Autonomic Neuroscience: Basic and Clinical 157 (2010) 24-30.

Cheung. The Mechanism of Acupuncture Therapy and Clinical Case Studies. Taylor and Francis, published in London. 2001. ISBN 0-415-27254-8. The Forward, Chapters 1-3, and 5.

"Acupuncture." http://en.wikipedia.org/wiki/Acupuncture.

Song, Kiseok, "The Compact Electro-Acupuncture System for Multi-Modal Feedback Electro-Acupuncture Treatment," 34th Annual International Conference of the IEEE EMBS, San Diego, CA, USA, Aug. 28-Sep. 1, 2012.

* cited by examiner

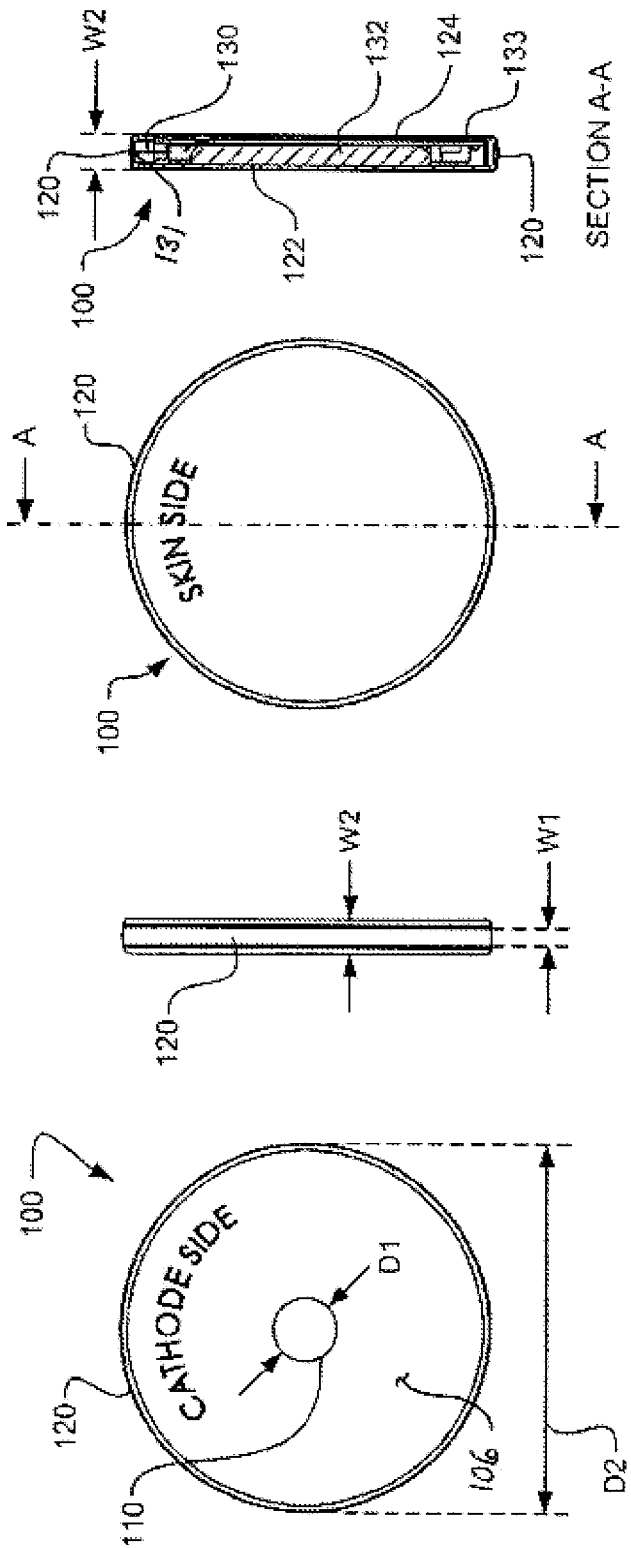

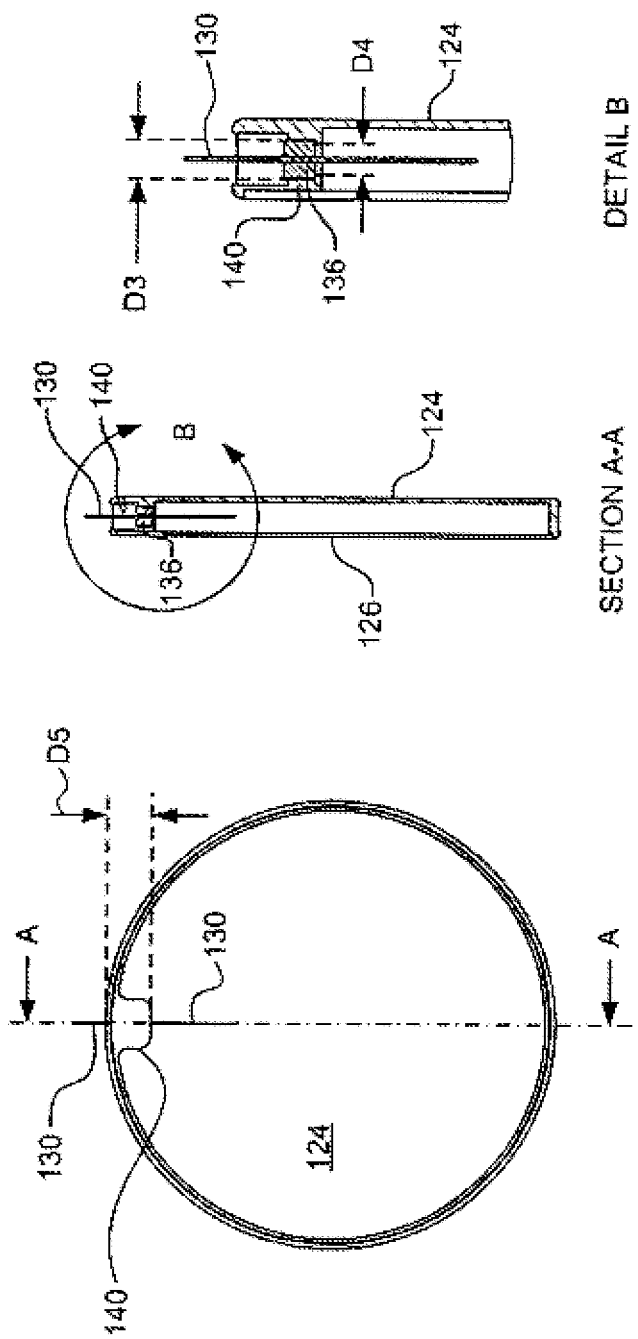

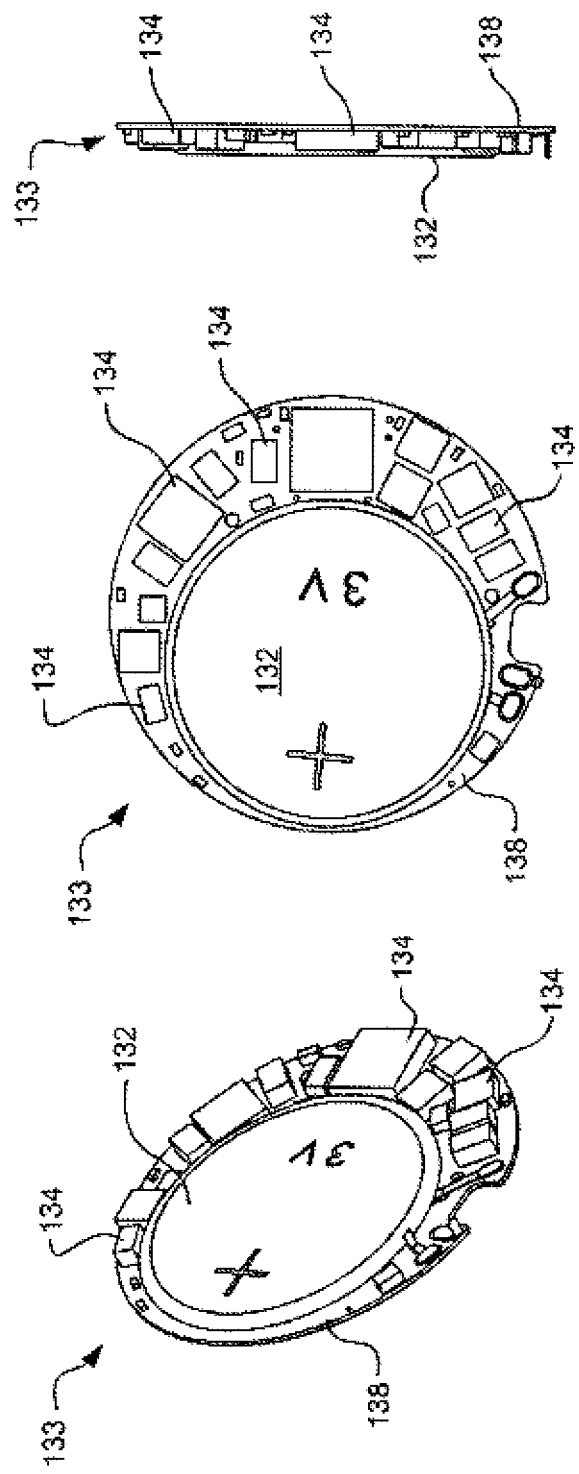

RADIAL FEED THROUGH PACKAGING FOR AN IMPLANTABLE ELECTROACUPUNCTURE DEVICE

RELATED APPLICATIONS

This application is a Continuation-In-Part (CIP) of U.S. patent application Ser. No. 13/598,582, filed Aug. 29, 2012, now published as U.S. Patent Application Publication No.: US 2014/0214115 A1, Pub. Date: Jul. 31, 2014 (hereinafter Applicant's "Parent Application"), which application is incorporated herein by reference in its entirety, including drawings and appendices. This application also claims the benefit of the following previously-filed provisional patent applications, each of which is also incorporated herein by reference:

1 Electrode Configuration For Implantable Electroacupuncture Device, Appl. No. 61/606,995, filed Mar. 6, 2012.
2 Radial Feed-Through For An Implantable Electroacupuncture Device, Appl. No. 61/676,275, filed Jul. 26, 2012.

BACKGROUND

The present disclosure describes a packaging configuration used for a small coin-sized electroacupuncture (EA) stimulator of the type described in the related applications referenced above, or equivalent small, thin, self-contained stimulators adapted for implantation under the skin. More particularly, the present disclosure relates to improvements in a radial feed-through pin that may be used as part of the packaging configuration of a small coin-sized, hermetically-sealed case that houses an implantable electroacupuncture device (IEAD), or equivalent electronic stimulation circuitry. Such feed-through pin provides a reliable and easy-to-manufacture electrical connection for use between electronic output circuitry of the IEAD housed within the coin-sized case, and an anode electrode secured to the outside of the case.

As indicated in the preceding paragraph, in an IEAD of the type disclosed in the applications referenced above, a feed-through pin is required to connect the electronics output from inside the hermetically-sealed, thin-profile, titanium or stainless steel implant case to a anode electrode on the outside of the case.

Note, as used herein, the term "feed-through" pin refers to the electrical conductive path made between electronic circuitry inside of an hermetically-sealed case, and to wires and/or electrodes on the outside of the hermetically-sealed case. The conductive path used to make such a feed-through path is typically a metal pin that passes through a bead of Ruby, ceramic (such as, e.g., Alumina) or glass or some other type of electrical-insulator material that is brazed or bonded to the metal case (to prevent the conductive pin from being electrically shorted to the metallic case). The electrically conductive pin thus feeds an insulated electrical connection through the metallic wall of the hermetically-sealed case, without being shorted to the metallic wall, while maintaining the hermeticity of the sealed case. Such a "feed-through pin" may also be referred to herein by many other, but equivalent terms. For example, the adjective phrase "feed-through" may be spelled different ways, such as "feedthrough", "feed through", "feed thru", or "feedthru", all used to modify the noun "pin", or "wire", or "conductor", or "conductive path", or "assembly", or similar terms. Sometimes, the adjective "feed-through", or variations thereof, is simply used as a noun. E.g., a feed-through pin or feed-through assembly may be referred to simply as a "feed through" or a "feedthru".

A major difficulty with placing a feed-through insulator and pin so that it passes through an hermetically sealed case wall is to keep the feed-through insulator and brazed joint a safe distance from where the metal case is welded, typically using laser seam welding. Otherwise, the feed-through insulator and the brazed interface, and its resulting assembly (of a Ruby or Ceramic (e.g., Alumina) bead or other insulative bead that surrounds the pin) can easily be damaged by the high temperatures associated with the welding.

Another difficulty associated with the location of the feed-through pin is the orientation of the feed-through pin relative to the case wall. For relatively thick cases, short feed-through pins can be placed in just about any location and orientation relative to the case wall. In such instance, it is thus a relatively straight forward design to place the feed-through pins as far away from the welded seams as possible to minimize any potential thermal damage during assembly and welding of the case. However, for thin cases, e.g., coin-size cases of the type used by an IEAD of the type described above, about the only option for placing a feed-through pin is to place it radially so as to pass through the perimeter edge of the case. However, such placement typically places the pin much too close to the welded seam of the case, and therefore subjects the pin assembly to very high, potentially damaging, temperatures when the case is welded closed.

What is needed, therefore, is a packaging configuration for a coin-sized hermetically-sealed case that allows a radial feed-through insulator and pin to be used, but that also protects such pin, insulator and brazed joint from dangerously high temperatures during the manufacturing process. Such a packaging configuration is described and claimed herein.

As background regarding the need for, design and use of an implantable electroacupuncture device (IEAD) of the type described in the references cited above, a brief history of acupuncture and electroacupuncture (EA) will next be presented.

Traditional acupuncture and acupressure has been practiced in Eastern civilizations (principally in China, but also in other Asian countries) for at least 2500 years. It is still practiced today throughout many parts of the world, including the United States and Europe. Acupuncture is an alternative medicine that treats patients by insertion and manipulation of needles in the body at selected points.

The locations where the acupuncture needles are inserted are referred to as "acupuncture points" or simply just "acupoints". The location of acupoints in the human body has been developed over thousands of years of acupuncture practice, and maps showing the location of acupoints in the human body are readily available in acupuncture books or online. An excellent reference book that identifies all of the traditional acupoints within the human body is *WHO STANDARD ACUPUNCTURE POINT LOCATIONS IN THE WESTERN PACIFIC REGION*, published by the World Health Organization (WHO), Western Pacific Region, 2008 (updated and reprinted 2009), ISBN 978 92 9061 248 7 (hereafter "*WHO Standard Acupuncture Point Locations* 2008"). The Table of Contents, Forward (page v-vi) and General Guidelines for Acupuncture Point Locations (pages 1-21) of the *WHO Standard Acupuncture Point Locations* 2008 are incorporated herein by reference.

Acupoints are typically identified by various letter/number combinations, e.g., L6, S37. The maps that show the location of the acupoints may also identify what condition, illness or deficiency the particular acupoint affects when manipulation of needles inserted at the acupoint is undertaken.

It is noted that references to the acupoints in the literature are not always consistent with respect to the format of the letter/number combination. Some acupoints are identified by a name only, e.g., Tongli. The same acupoint may be identified by others by the name followed with a letter/number combination placed in parenthesis, e.g., Tongli (HT5). Alternatively, the acupoint may be identified by its letter/number combination followed by its name, e.g., HT5 (Tongli). The first letter typically refers to a body organ, or other tissue location associated with, or affected by, that acupoint. However, usually only the letter is used in referring to the acupoint, but not always. Thus, for example, the acupoint ST40 is the same as acupoint Stomach 40 which is the same as ST-40 which is the same as ST 40 which is the same as Fenglong. For purposes of this patent application, unless specifically stated otherwise, all references to acupoints that use the same name, or the same first letter and the same number, and regardless of slight differences in second letters and formatting, are intended to refer to the same acupoint.

As an alternative to traditional acupuncture, some have proposed applying moderate electrical stimulation at selected acupuncture points through needles that have been inserted at those points. See, e.g., http://en.wikipedia.org/wiki/Electroacupuncture. Such electrical stimulation is known as electroacupuncture (EA). According to *Acupuncture Today*, a trade journal for acupuncturists: "Electroacupuncture is quite similar to traditional acupuncture in that the same points are stimulated during treatment. As with traditional acupuncture, needles are inserted on specific points along the body. The needles are then attached to a device that generates continuous electric pulses using small clips. These devices are used to adjust the frequency and intensity of the impulse being delivered, depending on the condition being treated. Electroacupuncture uses two needles at a time so that the impulses can pass from one needle to the other. Several pairs of needles can be stimulated simultaneously, usually for no more than 30 minutes at a time." "Acupuncture Today: Electroacupuncture". Feb. 1, 2004 (retrieved on-line Aug. 8, 2006 at http://www.acupuncturetoday.com/abc/electroacupuncture.php).

U.S. Pat. No. 6,735,475, issued to Whitehurst et al., discloses use of an implantable miniature neurostimulator, referred to as a "microstimulator," that can be implanted into a desired tissue location and used as a therapy for headache and/or facial pain. The microstimulator has a tubular shape, with electrodes at each end.

Other patents of Whitehurst et al. teach the use of this small, microstimulator, placed in other body tissue locations, including within an opening extending through the skull into the brain, for the treatment of a wide variety of conditions, disorders and diseases. See, e.g., U.S. Pat. No. 6,950,707 (obesity and eating disorders); U.S. Pat. No. 7,003,352 (epilepsy by brain stimulation); U.S. Pat. No. 7,013,177 (pain by brain stimulation); U.S. Pat. No. 7,155,279 (movement disorders through stimulation of Vagus nerve with both electrical stimulation and drugs); U.S. Pat. No. 7,292,890 (Vagus nerve stimulation); U.S. Pat. No. 7,203,548 (cavernous nerve stimulation); U.S. Pat. No. 7,440,806 (diabetes by brain stimulation); U.S. Pat. No. 7,610,100 (osteoarthritis); and U.S. Pat. No. 7,657,316 (headache by stimulating motor cortex of brain).

Techniques for using electrical devices, including external EA devices, for stimulating peripheral nerves and other body locations for treatment of various maladies are known in the art. See, e.g., U.S. Pat. Nos. 4,535,784; 4,566,064; 5,195,517; 5,250,068; 5,251,637; 5,891,181; 6,393,324; 6,006,134; 7,171,266; and 7,171,266. The methods and devices disclosed in these patents, however, typically utilize (i) large implantable stimulators having long leads that must be tunneled through tissue or blood vessels over an extended distance to reach the desired stimulation site, (ii) external devices that must interface with implanted electrodes via percutaneous leads or wires passing through the skin, or (iii) inefficient and power-consuming wireless transmission schemes. Unfortunately, in Applicant's view, such devices and methods are still far too invasive, or are ineffective, and/or are much too expensive, and thus do not provide a viable means for providing needed medical therapy for a patient.

From the above, it is seen that there is a need in the art for a more affordable, less invasive device and technique for electroacupuncture stimulation of acupoints that does not require the continual use of needles inserted through the skin, or long insulated wires implanted or inserted into blood vessels, for the purpose of treating an illness or deficiency of a patient.

SUMMARY

The above and other needs are addressed by the invention(s) disclosed herein. The invention provides a feed-through configuration having a radial pin arrangement, thereby enabling a thin profile implant. The feed-through pin assembly occupies a very small volume and thus provides more space for electronic circuitry, including a thin-profile coin-cell type battery, inside the case. Advantageously, the radially oriented feed-through pin assembly is integrated into, and forms an integral part of, the case assembly. The case assembly includes a radial recess at the edge of the case, wherein the feed-through pin is located. This helps thermally isolate the feed-through assembly from the laser beam weld at the edge of the case. Moreover, the case assembly used with the radial feed-through pin advantageously includes a ring electrode around the exterior edge of the case, thereby allowing electrical connection with the ring electrode to be easily made and secured simply by welding the distal end of the feed-through pin to the ring electrode.

One characterization of the invention described herein is an hermetically-sealed implantable electroacupuncture device (IEAD). Such IEAD includes (a) a case having a bottom and a side wall, the case having the form of a shallow container, closed at one end and open at the other end, the case being made from a biocompatible metal; (b) a recess formed as an integral part of the side wall at one location of the side wall, the recess extending into the space defined by the case a prescribed amount and having an opening in the bottom thereof; (c) a feed-through pin assembly comprising a feed-through pin embedded or brazed within an insulating material, the insulating material being hermetically brazed to the opening in the bottom of the recess, with a distal end of the feed-through pin extending radially outward beyond the side wall of the case, and with a proximal end of the feed-through pin extending radially inward towards the center of the volume within the case; (d) an electronic circuit assembly, including a battery, mounted inside of the case, with the proximal end of the feed-through pin being mechanically and electrically connected to a first designated output port of the electronic assembly, and with a second designated output port of the electronic assembly being connected to the case; (e) a cover plate hermetically bonded to the edges of the side walls of the case; (f) a first electrode comprising a plate bonded to the bottom of the case on the outside of the case; and (g) a second electrode comprising a ring electrode positioned around the side wall, an underneath side of the ring electrode being electrically connected to the distal tip of the feed-through pin at the location where the recess is formed.

Further included in the IEAD is an insulating layer of material positioned between the underneath side of the ring electrode and the side wall of the case, this insulating layer preventing the second electrode from electrically contacting the case. Additionally, an insulating layer of a biocompatible non-conductive material covers all portions of the outside of the case and cover plate except for exposed surface areas of the first electrode plate and the second electrode ring.

In operation, the IEAD thus described (in the previous two paragraphs) is implanted in a patient, and electroacupuncture stimulation pulses generated by the electronic circuit assembly are applied to body tissue of the patient with which the first and second electrodes of the IEAD are in contact when the IEAD is implanted within a patient.

The invention described herein may be further viewed as a method of assembling an implantable electroacupuncture device (IEAD) in a small, thin, hermetically-sealed, housing having a maximum linear dimension in a first plane of no more than 25 mm and a maximum linear dimension in a second plane orthogonal to the first plane of no more than 2.5 mm. Included within the housing is at least one feed-through pin assembly that radially passes through a wall of the thin housing and that isolates the feed-through pin assembly from high temperatures and residual weld stresses that it would otherwise be subjected to when the thin housing is welded shut to hermetically-seal its contents. The method of assembly includes the steps of:

(a) forming a thin housing having a bottom case and a top cover plate, the top cover plate being adapted to fit over the bottom case, the bottom case having a maximum linear dimension of no more than 25 mm;
(b) forming a recess in a wall of the housing;
(c) placing a feed-through assembly within the recess so that a feed-through pin of the feed-through assembly electrically passes through a wall of the recess at a location that is separated from where the wall of the housing is designed to contact the top cover plate; and
(d) welding the top cover plate to the bottom case around a perimeter of the bottom case, thereby hermetically sealing the bottom case and top case together.

BRIEF DESCRIPTION OF THE DRAWINGS

The above and other aspects, features and advantages of the invention will be more apparent from the following more particular description thereof, presented in conjunction with the following drawings. These drawings illustrate various embodiments of the principles described herein and are part of the specification. The illustrated embodiments are merely examples and do not limit the scope of the disclosure.

FIG. 2 shows a plan view of one surface (identified in FIG. 2 as the "Cathode Side") of the IEAD housing illustrated in FIG. 1.

FIG. 2A shows a side view of the IEAD housing illustrated in FIG. 1.

FIG. 3 shows a plan view of the other side, indicated as the "Skin Side," of the IEAD housing or case illustrated in FIG. 1.

FIG. 3A is a sectional view of the IEAD of FIG. 3 taken along the line A-A of FIG. 3.

FIG. 5 is a plan view of the empty IEAD housing shown in FIG. 4.

FIG. 5A depicts a sectional view of the IEAD housing of FIG. 5 taken along the section line A-A of FIG. 5.

FIG. 5B shows an enlarged view or detail of the portion of FIG. 5A that is encircled with the line B.

FIG. 6 is a perspective view of an electronic assembly, including a battery, adapted to fit inside of the empty housing of FIG. 4 and FIG. 5.

FIGS. 6A and 6B show a plan view and side view, respectively, of the electronic assembly shown in FIG. 6.

Figure 1:
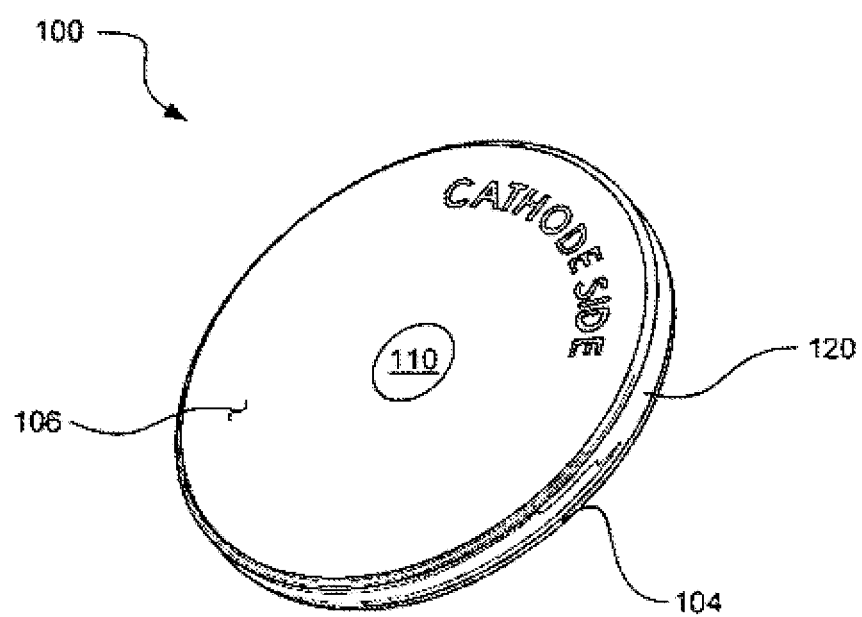
FIG. 1 is a perspective view of an Implantable Electroacupuncture Device (IEAD) made in accordance with the teachings presented herein.

Appendix A, submitted herewith, illustrates some examples of alternate symmetrical electrode configurations that may be used with an IEAD of the type described herein.

Appendix B, submitted herewith, illustrates a few examples of non-symmetrical electrode configurations that may be used with an IEAD made in accordance with the teachings herein.

Appendix C, submitted herewith, shows an example of the code used in the micro-controller IC (e.g., U2 in FIG. 11) to control the basic operation and programming of the IEAD, e.g., to turn the IEAD ON/OFF, adjust the amplitude of the stimulus pulse, and the like, using only an external magnet as an external communication element.

Appendices A, B and C are incorporated by reference herein.

Throughout the drawings, identical reference numbers designate similar, but not necessarily identical, elements.

DETAILED DESCRIPTION

Overview

As an overview, in a coin-sized implantable electroacupuncture device (IEAD) of the type disclosed in the applications referenced above, a feed-through connection is required to electrically connect the output of the electronic circuitry located inside of an hermetically-sealed, thin profile implant case (which is approximately only about 2.5 mm thick) to a ring-shaped anode electrode mounted on the cylindrical surface of the perimeter of the case.

Laser seam welding of the metal hermetic package creates a heat affected zone (as well as a mechanical shock zone) around the weld that can damage the hermeticity of the feed-through if it is too close to the weld. A single continuous laser seam weld close to the edge of the package case is desirable for simple and robust manufacturing. In order to maintain the thin package and efficient connection to the ring electrode, a radial orientation of a feed-through pin at the edge of the package case is also desirable. Yet, placing the feed-through pin at the edge of the package brings the laser seam weld at the outer edge of the case close to the feed-through pin and its associated assembly.

The present invention advantageously allows a very thin package to be produced by implementing a radial feed-through assembly configuration that allows the feed-through pin and insulator to be positioned at the edge of the package, yet keeps it sufficiently far from the laser seam weld in such a way so as not to be damaged by the heat affected zone during laser seam welding.

More particularly, as is evident from the diagrams and figures, and their accompanying descriptions presented herein, the feed-through assembly design of the present invention incorporates a radial recess at the edge of the IEAD package wherein the feed-through assembly is placed. The distal tip of the feed-through pin advantageously extends beyond the edge of the package where it can readily be attached to a ring electrode that fits over the edge of the package. Yet, the actual feed-through assembly, i.e., that more proximal portion of the feed-through pin or wire that is brazed and embedded within a ruby bead, or other insulating material, is in the bottom of the recess, and therefore sufficiently thermally and mechanically far away from the high temperatures associated with a laser seam weld when the welding is performed.

In the description that follows, many of the meticulous details associated with the manufacture and assembly of the device described are not provided. This is because such details should be known, it is submitted, by a person of skill in the art (e.g., a person in the electrical/electronics, bioengineering, mechanical, materials and medical arts). In particular, in combination with the teachings presented herein, the person of skill in the art should be able to readily discern how the feed-through assembly described herein is manufactured, and how such assembly is then incorporated into the overall hermetically-sealed package design of the described device, e.g., a particular embodiment of an implantable electroacupuncture device, or IEAD.

Definitions

As used herein, "annular", "circumferential", "circumscribing", "surrounding" or similar terms used to describe an electrode or electrode array, or electrodes or electrode arrays, (where the phrase "electrode or electrode array," or "electrodes or electrode arrays," is also referred to herein as "electrode/array," or "electrodes/arrays," respectively) refers to an electrode/array shape or configuration that surrounds or encompasses a point or object, such as another electrode, without limiting the shape of the electrode/array or electrodes/arrays to be circular or round. In other words, an "annular" electrode/array (or a "circumferential" electrode/array, or a "circumscribing" electrode/array, or a "surrounding" electrode/array), as used herein, may be many shapes, such as oval, polygonal, starry, wavy, and the like, including round or circular.

"Nominal" or "about" when used with a mechanical dimension, e.g., a nominal diameter of 23 mm, means that there is a tolerance associated with that dimension of no more than plus or minus (+/−) 5%. Thus, a dimension that is nominally 23 mm means a dimension of 23 mm+/−1.15 mm (0.05× 23 mm=1.15 mm).

"Nominal" when used to specify a battery voltage is the voltage by which the battery is specified and sold. It is the voltage you expect to get from the battery under typical conditions, and it is based on the battery cell's chemistry. Most fresh batteries will produce a voltage slightly more than their nominal voltage. For example, a new nominal 3 volt lithium coin-sized battery will measure more than 3.0 volts, e.g., up to 3.6 volts under the right conditions. Since temperature affects chemical reactions, a fresh warm battery will have a greater maximum voltage than a cold one. For example, as used herein, a "nominal 3 volt" battery voltage is a voltage that may be as high as 3.6 volts when the battery is brand new, but is typically between 2.7 volts and 3.4 volts, depending upon the load applied to the battery (i.e., how much current is being drawn from the battery) when the measurement is made and how long the battery has been in use.

As explained in more detail below, an important aspect of the invention recognizes that an electroacupuncture modulation scheme, or other tissue stimulation scheme, need not be continuous, thereby allowing the implanted device to use a small, high density, power source to provide such non-continuous modulation. (Here, it should be noted that "modulation," as that phrase is used herein, is the application of electrical stimulation pulses, at low intensities, low frequencies and low duty cycles, to at least one of the target stimulation sites, e.g., an acupuncture site that has been identified as affecting a particular condition of a patient.) As a result, the device can be very small. And, because the electrodes typically form an integral part of the housing of the device, the device may thus be implanted directly at (or very near to) the desired target tissue location.

Mechanical Design

Turning to FIG. 1, a preferred configuration of a small, implantable, electroacupuncture device will next be described. As seen in FIG. 1, a preferred implantable electroacupuncture device (IEAD) 100 is shown in perspective view. Such device is designed to be used to treat a disease, deficiency, or other medical condition of a patient. The IEAD 100 may also sometimes be referred to as an implantable electroacupuncture stimulator (IEAS). As seen in FIG. 1, the IEAD 100 has the appearance of a disc or coin, having a front side 106 (which is also labeled as the "Cathode Side") 106, a back side (also referred to as the "Skin Side") 102 (which skin side is not visible in FIG. 1) and an edge side 104.

As used herein, the "front" side of the IEAD 100 is the side that is positioned so as to face the target stimulation point (e.g., the desired acupoint) where EA stimulation is to be applied when the IEAD is implanted. The "back" side is the side opposite the front side and is the farthest away from the target stimulation point when the IEAD is implanted, and is usually the side closest to the patient's skin. The "edge" of the IEAD is the side that connects or joins the front side to the back side. In FIG. 1, the IEAD 100 is oriented to show the front side 102 and a portion of the edge side 104.

It should be noted here that throughout this description, the terms IEAD 100, IEAD housing 100, bottom case 124, can 124, or IEAD case 124, or similar terms, are used to describe the housing structure of the EA device. In some instances it may appear these terms are used interchangeably. However, the context should dictate what is meant by these terms. As the drawings illustrate, particularly FIG. 7, there is a bottom case 124 that comprises the "can" or "container" wherein the components of the IEAD 100 are first placed and assembled during manufacture of the IEAD 100. When all of the components are assembled and placed within the bottom case 124, a cover plate 122 is welded to the bottom case 124 to form the hermetically-sealed housing of the IEAD. The cathode electrode 110 is attached to the outside of the bottom case 124 (which is the front side 102 of the device), and the ring anode electrode 120 is attached, along with its insulating layer 129, around the perimeter edge 104 of the bottom case 124. Finally, a layer of silicone molding 125 covers the IEAD housing except for the outside surfaces of the anode ring electrode and the cathode electrode.

Figure 7:
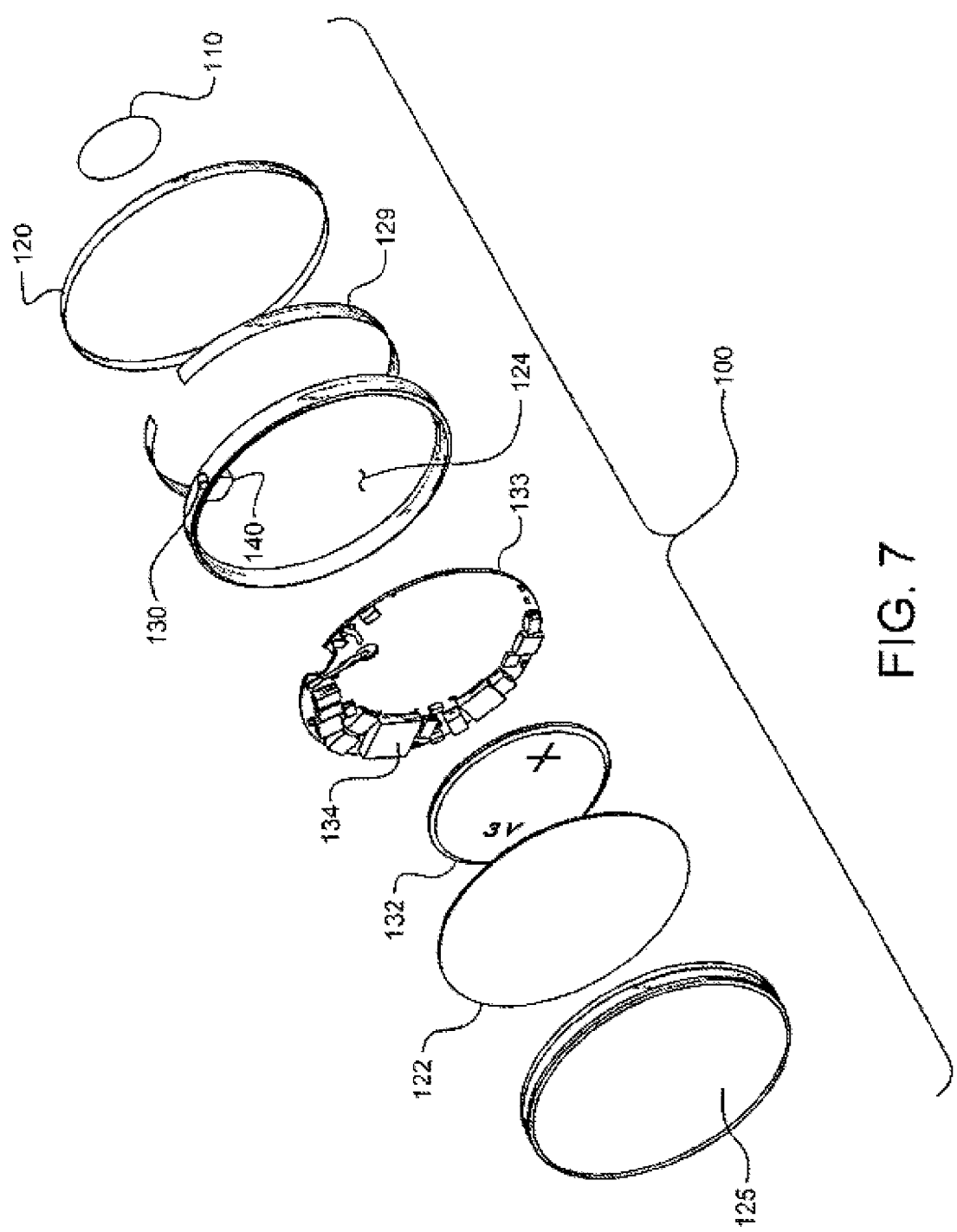
FIG. 7 is an exploded view of the IEAD assembly, illustrating its constituent parts.

The embodiment of the IEAD 100 shown in FIG. 1 utilizes two electrodes, a cathode electrode 110 that is centrally positioned on the front side 102 of the IEAD 100, and an anode electrode 120. The anode electrode 120 is a ring electrode that fits around the perimeter edge 104 of the IEAD 100. Not visible in FIG. 1, but which is described hereinafter in connection with the description of FIG. 7, is a layer of insulating material 129 that electrically insulates the anode ring electrode 120 from the perimeter edge 104 of the housing or case 124.

Not visible in FIG. 1, but a key feature of the mechanical design of the IEAD 100, is the manner in which an electrical connection is established between the ring electrode 120 and electronic circuitry carried inside of the IEAD 100. This electrical connection is established using a radial feed-through pin that fits within a recess formed in a segment of the edge of the case 124, as explained more fully below in connection with the description of FIGS. 5, 5A, 5B and 7.

In contrast to the feed-through pin that establishes electrical contact with the anode electrode, electrical connection with the cathode electrode 110 is established simply by forming or attaching the cathode electrode 110 to the front surface 102 of the IEAD case 124. In order to prevent the entire case 124 from functioning as the cathode (which is done to better control the electric fields established between the anode and cathode electrodes), the entire IEAD housing is covered in a layer of silicone molding 125 (see FIG. 7), except for the outside surface of the anode ring electrode 120 and the cathode electrode 110.

The advantage of using a central cathode electrode and a ring anode electrode is described in U.S. Provisional Patent Application No. 61/672,257, filed 6 Mar. 2012, entitled "Electrode Configuration for Implantable Electroacupuncture Device", which application is incorporated herein by reference. One significant advantage of this electrode configuration is that it is symmetrical. That is, when implanted, the surgeon or other medical personnel performing the implant procedure, need only assure that the cathode side of the IEAD 100, which (for the embodiment shown in FIGS. 1-7) is the front side of the device, faces the target tissue location that is to be stimulated. In addition, the IEAD must be implanted over the desired acupoint, or other tissue location, that is intended to receive the electroacupuncture (EA) stimulation. The orientation of the IEAD 100 is otherwise not important.

Figure 1A:
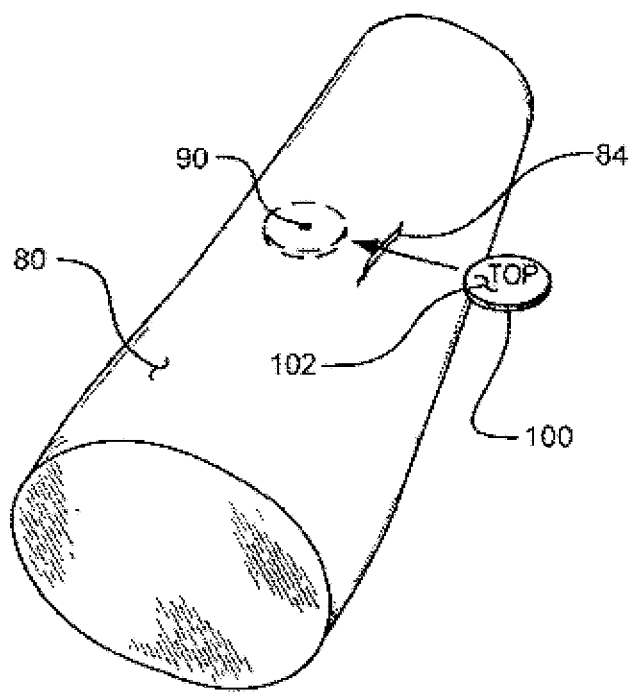
FIG. 1A illustrates the location of an exemplary target tissue stimulation site, e.g., an acupoint, whereat the IEAD of FIG. 1 may be implanted for the treatment of a particular disease or condition.

FIG. 1A illustrates the location of an exemplary target stimulation point 90, e.g. a point on a limb 80 of the patient, whereat the IEAD of FIG. 1 may be implanted for the treatment of a particular disease or condition of the patient. Such location is representative of a wide variety of acupoints, or other target tissue locations, whereat the IEAD of FIG. 1 could be implanted.

Figure 1B:
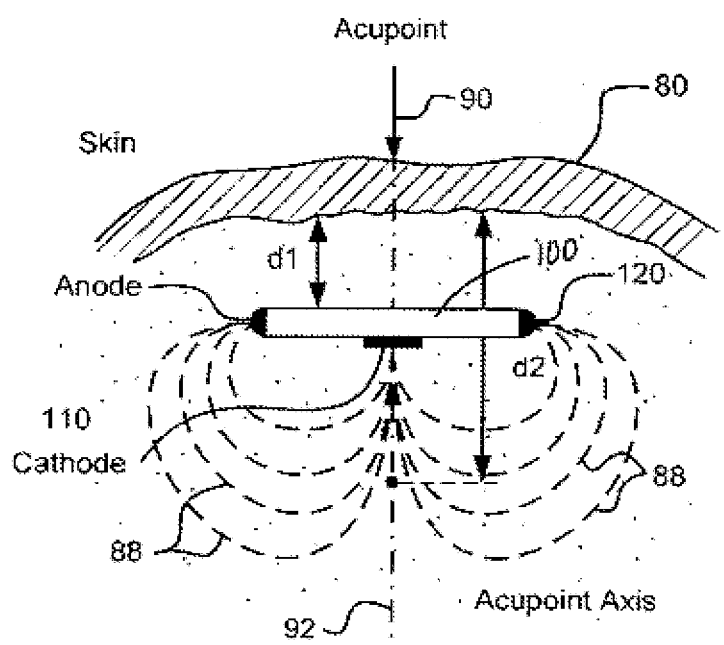
FIG. 1B shows a sectional view of an IEAD implanted at a selected target stimulation site, and illustrates the electric field gradient lines created when an electroacupuncture (EA) pulse is applied to the tissue through the central electrode and ring electrode attached to the bottom surface and perimeter edge, respectively, of the IEAD housing.

An implanted IEAD 100 is illustrated generally in FIG. 1B. Shown in FIG. 1B is a sectional view of a limb 80 of the patient wherein an acupoint 90 has been identified that is to receive acupuncture treatment (in this case electroacupuncture treatment). An incision (not shown in FIG. 1B) is made into the limb 80 a short distance, e.g., 10-15 mm, away from the acupoint 90. A slot (parallel to the limb) is formed at the incision by lifting the skin closest to the acupoint up at the incision. As necessary, the surgeon may form a pocket under the skin at the acupoint location. The IEAD 100, with its top side 102 being closest to the skin (and thus also referred to as the "Skin Side"), is then slid through the slot 84 into the pocket so that the center of the IEAD is located under the acupoint 90 on the skin surface. This implantation process is as easy as inserting a coin into a slot. With the IEAD 100 in place, the incision is sewn or otherwise closed, leaving the IEAD 100 under the skin 80 at the location of the acupoint 90 where electroacupuncture (EA) stimulation is desired.

In this regard, it should be noted that while the target stimulation point is generally identified by an "acupoint," which is typically shown in drawings and diagrams as residing on the surface of the skin, the surface of the skin is not the actual target stimulation point. Rather, whether such stimulation comprises manual manipulation of a needle inserted through the skin at the location on the skin surface identified as an "acupoint", or whether such stimulation comprises electrical stimulation applied through an electrical field oriented to cause stimulation current to flow through the tissue at a prescribed depth below the acupoint location on the skin surface, the actual target tissue point to be stimulated is located beneath the skin at a depth d2 that varies depending on the particular acupoint location. When stimulation is applied at the target tissue point, such stimulation is effective at treating a selected condition of the patient, e.g., high cholesteral, because there is something in the tissue at that location, or near that location, such as a nerve, a tendon, a muscle, or other type of tissue, that responds to the applied stimulation in a manner that contributes favorably to the treatment of the condition experienced by the patient.

FIG. 1B illustrates a sectional view of the IEAD 100 implanted so as to be centrally located under the skin at the selected acupoint 90, and over the acupoint axis line 92. Usually, for most patients, the IEAD 100 is implanted at a depth d1 of approximately 2-4 mm under the skin. The top (skin) side 102 of the IEAD is nearest to the skin 80 of the patient. The bottom (cathode) side 106 of the IEAD, which is the side on which the central cathode electrode 110 resides, is farthest from the skin. Because the cathode electrode 110 is centered on the bottom of the IEAD, and because the IEAD 100 is implanted so as to be centered under the location on the skin where the acupoint 90 is located, the cathode 110 is also centered over the acupoint axis line 92.

FIG. 1B further illustrates the electric field gradient lines 88 that are created in the body tissue 86 surrounding the acupoint 90 and the acupoint axis line 92. (Note: for purposes herein, when reference is made to providing EA stimulation at a specified acupoint, it is understood that the EA stimulation is provided at a depth of approximately d2 below the location on the skin surface where the acupoint is indicated as being located.) As seen in FIG. 1B, the electric field gradient lines are strongest along a line that coincides with, or is near to, the acupoint axis line 92. It is thus seen that one of the main advantages of using a symmetrical electrode configuration that includes a centrally located electrode surrounded by an annular electrode is that the precise orientation of the IEAD within its implant location is not important. So long as one electrode is centered over the desired target location, and the other electrode surrounds the first electrode (e.g., as an annular electrode), a strong electric field gradient is created that is aligned with the acupoint axis line. This causes the EA stimulation current to flow along (or very near) the acupoint axis line 92, and will result in the desired EA stimulation in the tissue at a depth d2 below the acupoint location indicated on the skin.

FIG. 2 shows a plan view of the "front" (or "cathode") side 106 of the IEAD 100. As seen in FIG. 2, the cathode electrode 110 appears as a circular electrode, centered on the front side, having a diameter D1. The IEAD housing has a diameter D2 and an overall thickness or width W2. For the preferred embodiment shown in these figures, D1 is about 4 mm, D2 is about 23 mm and W2 is a little over 2 mm (2.2 mm). The value of D1 may vary as a function of the type of material from which it is made, e.g., stainless steel or platinum or some other biocompatible material, and the anticipated current density that must flow through the electrode for the particular application with which the IEAD is being used. See Applicant's copending patent application, incorporated herein by reference, application Ser. No. 13/776,155, filed 25 Feb. 2013, Electrode Configuration for Implantable Electroacupuncture Device, for a more detailed description of how the size and type of material used for the electrode(s) affects the current density that can be obtained using such electrode size and material.

FIG. 2A shows a side view of the IEAD 100. The ring anode electrode 120, best seen in FIG. 2A, has a width W1 of about 1.0 mm, or approximately ½ of the width W2 of the IEAD.

FIG. 3 shows a plan view of the "back" (or "skin") side of the IEAD 100. As will be evident from subsequent figure descriptions, e.g., FIGS. 5A and 5B, the back side of the IEAD 100 comprises a cover plate 122 that is welded in place once the bottom case 124 has all of the electronic circuitry, and other components, placed inside of the housing.

FIG. 3A is a sectional view of the IEAD 100 of FIG. 1 taken along the line A-A of FIG. 3. Visible in this sectional view is the feed-through pin 130, including the distal end 131 of the feed-through pin 130 attached to the ring anode electrode 120. Also visible in this section view is an electronic assembly 133 on which various electronic components are mounted, including a disc-shaped battery 132. FIG. 3A further illustrates how the cover plate 122 is welded, or otherwise bonded, to the bottom case 124 in order to form the hermetically-sealed IEAD housing 100.

Figure 4:
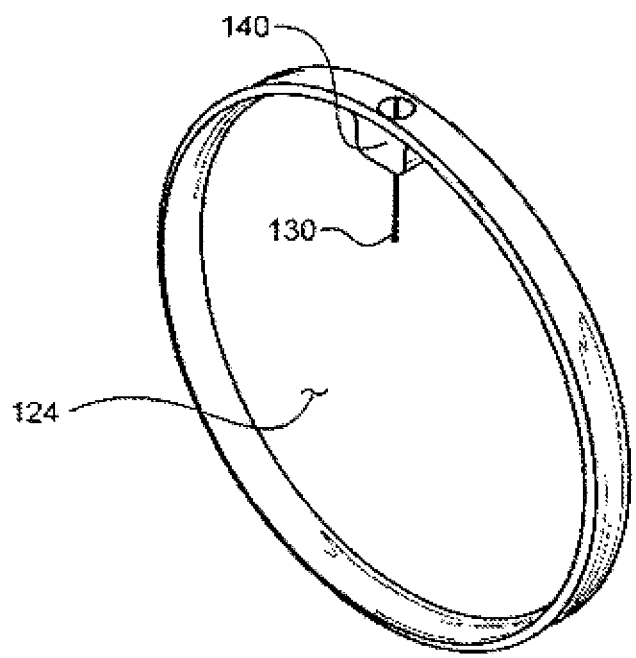
FIG. 4 is a perspective view of the IEAD housing, including a feed-through pin, before the electronic components are placed therein, and before being sealed with a cover plate.

FIG. 4 shows a perspective view of the IEAD case 124, including the feed-through pin 130, before the electronic components are placed therein, and before being sealed with the "skin side" cover plate 122. The case 124 is similar to a shallow "can" without a lid, having a short side wall around its perimeter. Alternatively, the case 124 may be viewed as a short cylinder, closed at one end but open at the other. (Note, in the medical device industry the housing of an implanted device is often referred to as a "can".) The feed-through pin 130 passes through a segment of the wall of the case 124 that is at the bottom of a recess 140 formed in the wall. The use of this recess 140 to hold the feed-through pin 130 is a key feature of the invention because it keeps the temperature-sensitive portions of the feed-through assembly (those portions that could be damaged by excessive heat) away from the thermal shock and residual weld stress inflicted upon the case 124 when the cover plate 122 is welded thereto.

Figure 4A:
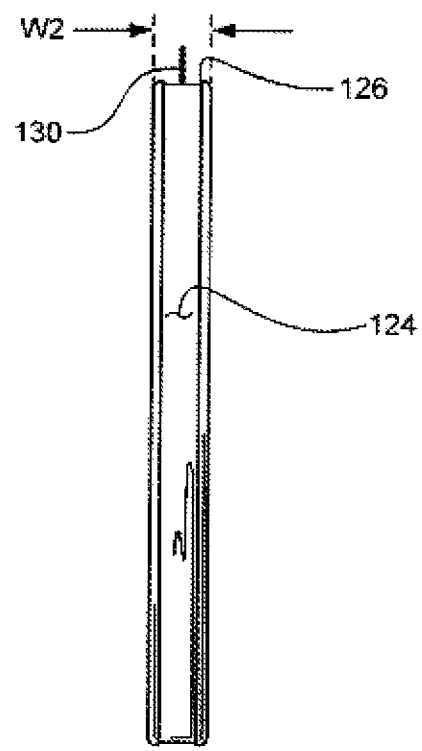
FIG. 4A is a side view of the IEAD housing of FIG. 4.

FIG. 4A is a side view of the IEAD case 124, and shows an annular rim 126 formed on both sides of the case 124. The ring anode electrode 120 fits between these rims 126 once the ring electrode 120 is positioned around the edge of the case 124. (This ring electrode 120 is, for most configurations, used as an anode electrode. Hence, the ring electrode 120 may sometimes be referred to herein as a ring anode electrode. However, it is noted that the ring electrode could also be employed as a cathode electrode, if desired.) A silicone insulator layer 129 (see FIG. 7) is placed between the backside of the ring anode electrode 120 and the perimeter edge of the case 124 where the ring anode electrode 120 is placed around the edge of the case 124.

FIG. 5 shows a plan view of the empty IEAD case 124 shown in the perspective view of FIG. 4. An outline of the recess cavity 140 is also seen in FIG. 5, as is the feed-through pin 130. A bottom edge of the recess cavity 140 is located a distance D5 radially inward from the edge of the case 124. In one embodiment, the distance D5 is between about 2.0 to 2.5 mm. The feed-through pin 130, which is just a piece of solid wire, is shown in FIG. 5 extending radially outward from the case 124 above the recess cavity 140 and radially inward from the recess cavity towards the center of the case 124. The length of this feed-through pin 130 is trimmed, as needed, when a distal end (extending above the recess) is connected (welded) to the anode ring electrode 120 (passing through a hole in the ring electrode 120 prior to welding) and when a proximal end of the feed-through pin 130 is connected to an output terminal of the electronic assembly 133.

FIG. 5A depicts a sectional view of the IEAD housing 124 of FIG. 5 taken along the section line A-A of FIG. 5. FIG. 5B shows an enlarged view or detail of the portion of FIG. 5A that is encircled with the line B. Referring to FIGS. 5A and 5B jointly, it is seen that the feed-through pin 130 is embedded within an insulator material 136, which insulating material 136 has a diameter of D3. The feed-through pin assembly (which pin assembly comprises the combination of the pin 130 embedded into the insulator material 136) resides on a shoulder around an opening or hole formed in the bottom of the recess 140 having a diameter D4. For the embodiment shown in FIGS. 5A and 5B, the diameter D3 is 0.95-0.07 mm, where the −0.07 mm is a tolerance. (Thus, with the tolerance considered, the diameter D3 may range from 0.88 mm to 0.95 mm) The diameter D4 is 0.80 mm with a tolerance of −0.06 mm. (Thus, with the tolerance considered, the diameter D4 could range from 0.74 mm to 0.80 mm).

The feed-through pin 130 is preferably made of pure platinum 99.95% or platinum iridium. A preferred material for the insulator material 136 is Ruby or alumina. The IEAD case 124, and the cover 122, are preferably made from titanium. The feed-through assembly, including the feed-through pin 130, ruby/alumina insulator 136 and the case 124 are hermetically sealed as a unit by gold brazing. Alternatively, active metal brazing can be used. (Active metal brazing is a form of brazing which allows metal to be joined to ceramic without metallization.)

The hermeticity of the sealed IEAD housing is tested using a helium leak test, as is common in the medical device industry. The helium leak rate should not exceed 1×10−9 STD cc/sec at 1 atm pressure. Other tests are performed to verify the case-to-pin resistance (which should be at least 15×106 Ohms at 100 volts DC), the avoidance of dielectric breakdown or flashover between the pin and the case 124 at 400 volts AC RMS at 60 Hz and thermal shock.

One important advantage provided by the feed-through assembly shown in FIGS. 4A, 5, 5A and 5B is that the feed-through assembly made from the feed-through pin 130, the ruby insulator 136 and the recess cavity 140 (formed in the case material 124) may be fabricated and assembled before any other components of the IEAD 100 are placed inside of the IEAD case 124. This advantage greatly facilitates the manufacture of the IEAD device.

Figure 5D:
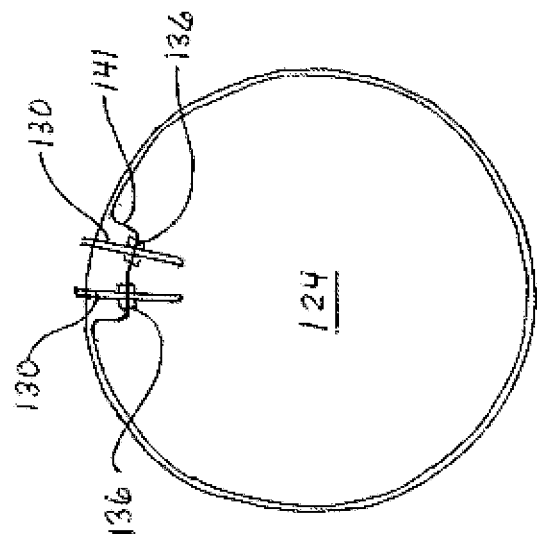
FIG. 5D is a plan view similar to FIG. 5 showing the use of multiple radial feed-through pins passing through the bottom of a single recess cavity.
Figure 5C:
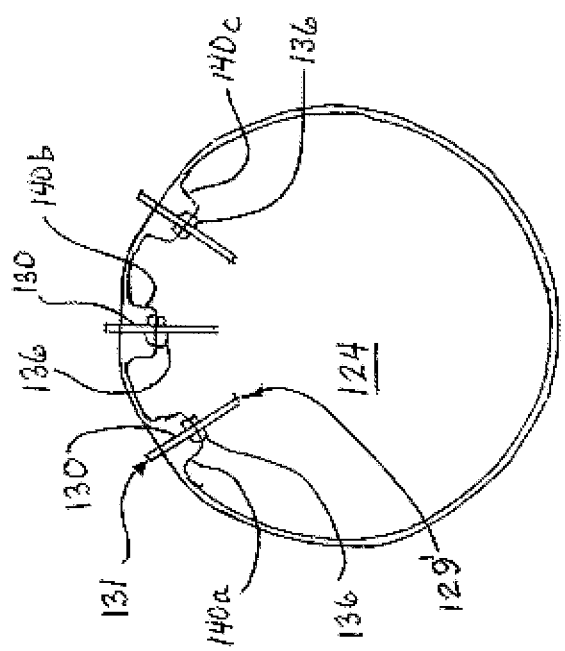
FIG. 5C is a plan view similar to FIG. 5 showing the use of multiple recess cavities in the IEAD housing, each with its own respective radial feed-through pin passing through the bottom of its recess cavity.

Next, with reference to FIGS. 5C and 5D, some alternate embodiments showing the use of multiple feed-through pins with the case 124 are illustrated. Two such embodiments are shown. In a first alternate embodiment, shown in FIG. 5C, multiple recess cavities 140 are formed in the case 124. That is, as seen in FIG. 5C, and with respect to the orientation of the case shown in FIG. 5C, a first recess cavity 140*a* is on the left side of the case (approximately at the 11:00 o'clock position), a second recess cavity 140*b* is in the middle of the case (approximately at the 12:00 o'clock position), and a third recess cavity 140*c* is on the right side of the case (approximately at the 1:00 o'clock position). Each of these multiple recess cavities, 140*a*, 140*b* and 140*c*, have a respective feed-through pin 130, with insulator material 136, passing through an opening in the bottom of their respective recess cavities. When initially assembled, each feed-through pin 130 has a distal tip 131 that extends radially outward beyond the perimeter edge of the case 124. The distal tip 131 can be trimmed to a suitable length, as needed, in order to connect it to its electrode. Likewise, a proximal end 129' of each feed-through pin 130 extends radially inward toward the center of the case 124. This proximal end 129' can similarly be trimmed, as required, in order to connect it to an appropriate location on the electronic assembly 133 or other location within the case 124.

In a second alternate embodiment, shown in FIG. 5D, multiple feed-through pins 130 are placed through a respective opening in the bottom of a single recess cavity 141. Two such feed-through pins 130, each with respective insulator material 136, are illustrated in FIG. 5D, but this number is only exemplary.

Turning next to FIG. 6, there is shown a perspective view of an electronic assembly 133. The electronic assembly 133 includes a multi-layer printed circuit (pc) board 138, or equivalent mounting structure, on which a battery 132 and various electronic components 134 are mounted. This assembly is adapted to fit inside of the empty bottom housing 124 of FIG. 4 and FIG. 5.

FIGS. 6A and 6B show a plan view and side view, respectively, of the electronic assembly 133 shown in FIG. 6. The electronic components are assembled and connected together so as to perform the circuit functions needed for the IEAD 100 to perform its intended functions. These circuit functions are explained in more detail below under the sub-heading "Electrical Design". Additional details associated with these functions may also be found in the co-pending patent applications referenced above.

FIG. 7 shows an exploded view of the complete IEAD 100, illustrating its main constituent parts. As seen in FIG. 7, the IEAD 100 includes, starting on the right and going left, a cathode electrode 110, a ring anode electrode 120, an insulating layer 129, the bottom case 124 (the "can" portion of the IEAD housing, and which includes the feed-through pin 130 which passes through an opening in the bottom of the recess 140 formed as part of the case, but wherein the feed-through pin 130 is insulated and does not make electrical contact with the metal case 124 by the ruby insulator 136), the electronic assembly 133 (which includes the battery 132 and various electronic components 134 mounted on a pc board 138) and the cover plate 122. The cover plate 122 is welded to the edge of the bottom case 124 using laser beam welding, or some equivalent process, as one of the final steps in the assembly process.

Other components included in the IEAD assembly, but not necessarily shown or identified in FIG. 7, include adhesive patches for bonding the battery 132 to the pc board 138 of the electronic assembly 133, and for bonding the electronic assembly 133 to the inside of the bottom of the case 124. To prevent high temperature exposure of the battery 132 during the assembly process, conductive epoxy is used to connect a battery terminal to the pc board 138. Because the curing temperature of conductive epoxy is 125° C., the following process is used: (a) first cure the conductive epoxy of a battery terminal ribbon to the pc board without the battery, (b) then glue the battery to the pc board using room temperature cure silicone, and (c) laser tack weld the connecting ribbon to the battery.

Also not shown in FIG. 7 is the manner of connecting the proximal end of the feed-through pin 130 to the pc board 138, and connecting a pc board ground pad to the case 124. A preferred method of making these connections is to use conductive epoxy and conductive ribbons, although other connection methods known in the art may also be used.

Further shown in FIG. 7 is a layer of silicon molding 125 that is used to cover all surfaces of the entire IEAD 100 except for the anode ring electrode 120 and the circular cathode electrode 110. An overmolding process is used to accomplish this, although overmolding using silicone LSR 70 (curing temperature of 120° C.) with an injection molding process cannot be used. Overmolding processes that may be used include: (a) molding a silicone jacket and gluing the jacket onto the case using room temperature cure silicone (RTV) inside of a mold, and curing at room temperature; (b) injecting room temperature cure silicone in a PEEK or Teflon® mold (silicone will not stick to the Teflon® or PEEK material); or (c) dip coating the IEAD 100 in room temperature cure silicone while masking the electrode surfaces that are not to be coated. (Note: PEEK is a well known semicrystalline thermoplastic with excellent mechanical and chemical resistance properties that are retained at high temperatures.)

When assembled, the insulating layer 129 is positioned underneath the ring anode electrode 120 so that the anode electrode does not short to the case 124. The only electrical connection made to the anode electrode 120 is through the distal tip of the feed-through pin 130. The electrical contact with the cathode electrode 110 is made through the case 124. However, because the entire IEAD is coated with a layer of silicone molding 125, except for the anode ring electrode 120 and the circular cathode electrode 110, all stimulation current generated by the IEAD 100 must flow between the exposed surfaces of the anode and cathode.

It is noted that while the preferred configuration described herein uses a ring anode electrode 120 placed around the edges of the IEAD housing, and a circular cathode electrode 110 placed in the center of the cathode side of the IEAD case 124, such an arrangement could be reversed, i.e., the ring electrode could be the cathode, and the circular electrode could be the anode.

Moreover, the location and shape of the electrodes may be configured differently than is shown in the one preferred embodiment described above in connection with FIGS. 1, and 2-7. For example, the ring anode electrode 120 need not be placed around the perimeter of the device, but such electrode may be a flat circumferential electrode that assumes different shapes (e.g., round or oval) that is placed on the front or back surface of the IEAD so as to surround the central electrode. Further, for some embodiments, the surfaces of the anode and cathode electrodes may have convex surfaces.

It is also noted that while one preferred embodiment has been disclosed herein that incorporates a round, or short cylindrical-shaped housing, also referred to as a coin-shaped housing, the invention does not require that the case 124 (which may also be referred to as a "container"), and its associated cover plate 122, be round. The case could just as easily be an oval-shaped, rectangular-shaped (e.g., square with smooth corners), polygonal-shaped (e.g., hexagon-, octagon-, pentagon-shaped), button-shaped (with convex top or bottom for a smoother profile) device. Any of these alternate shapes, or others, would still permit the basic principles of the invention to be used to provide a robust, compact, thin, case to house the electronic circuitry and power source used by the invention; as well as to help protect a feed-through assembly from being exposed to excessive heat during assembly, and to allow the thin device to provide the benefits described herein related to its manufacture, implantation and use. For example, as long as the device remains relatively thin, e.g., no more than about 2-3 mm, and does not have a maximum linear dimension greater than about 25 mm, then the device can be readily implanted in a pocket over the tissue area where the selected acupoint(s) is located. As long as there is a recess in the wall around the perimeter of the case wherein the feed-through assembly may be mounted, which recess effectively moves the wall or edge of the case inwardly into the housing a safe thermal distance, as well as a safe residual weld stress distance, from the perimeter wall where a hermetically-sealed weld occurs, the principles of the invention apply.

Further, it should be noted that while the preferred configuration of the IEAD described herein utilizes a central electrode on one of its surfaces that is round, having a diameter of nominally 4 mm, such central electrode need not necessarily be round. It could be oval shaped, polygonal-shaped, or shaped otherwise, in which case its size is best defined by its maximum width, which will generally be no greater than about 7 mm.

Finally, it is noted that the electrode arrangement may be modified somewhat, and the desired attributes of the invention may still be achieved. For example, as indicated previously, one preferred electrode configuration for use with the invention utilizes a symmetrical electrode configuration, e.g., an annular electrode of a first polarity that surrounds a central electrode of a second polarity. Such a symmetrical electrode configuration makes the implantable electroacupuncture device (IEAD) relatively immune to being implanted in an improper orientation relative to the body tissue at the selected acupoint(s) that is being stimulated. However, an electrode configuration that is not symmetrical may still be used and many of the therapeutic effects of the invention may still be achieved. For example, two spaced-apart electrodes on a front surface of the housing, one of a first polarity, and a second of a second polarity, could still, when oriented properly with respect to a selected acupoint tissue location, provide some desired therapeutic results.

As has already been mentioned, the shape of the circumferential electrode/array, whether circular, oval, or other shape, need not necessarily be the same shape as the IEAD housing, unless the circumferential electrode/array is attached to a perimeter edge of the IEAD housing. The IEAD housing may be round, or it may be oval, or it may have a polygon shape, or other shape, as needed to suit the needs of a particular manufacturer and/or patient.

Additional electrode configurations, both symmetrical electrode configurations and non-symmetrical electrode configurations, that may be used with an EA stimulation device as described herein, are illustrated in Appendix A and Appendix B.

Electrical Design

Next, with reference to FIGS. 8-14, the electrical design and operation of the circuits employed within the IEAD 100 will be briefly described. In particular, a description of the circuits that are used within the IEAD 100 will be described, which circuits, in combination with the packaging of the IEAD as described above in connection with FIGS. 1-7, allow the IEAD to perform its intended function. More details associated with the design of the electrical circuits described herein may be found in previously-filed U.S. patent application Ser. No. 13/598,582, filed Aug. 29, 2012, entitled Implantable Electroacupuncture System and Method for Reducing Hypertension.

Figure 8:
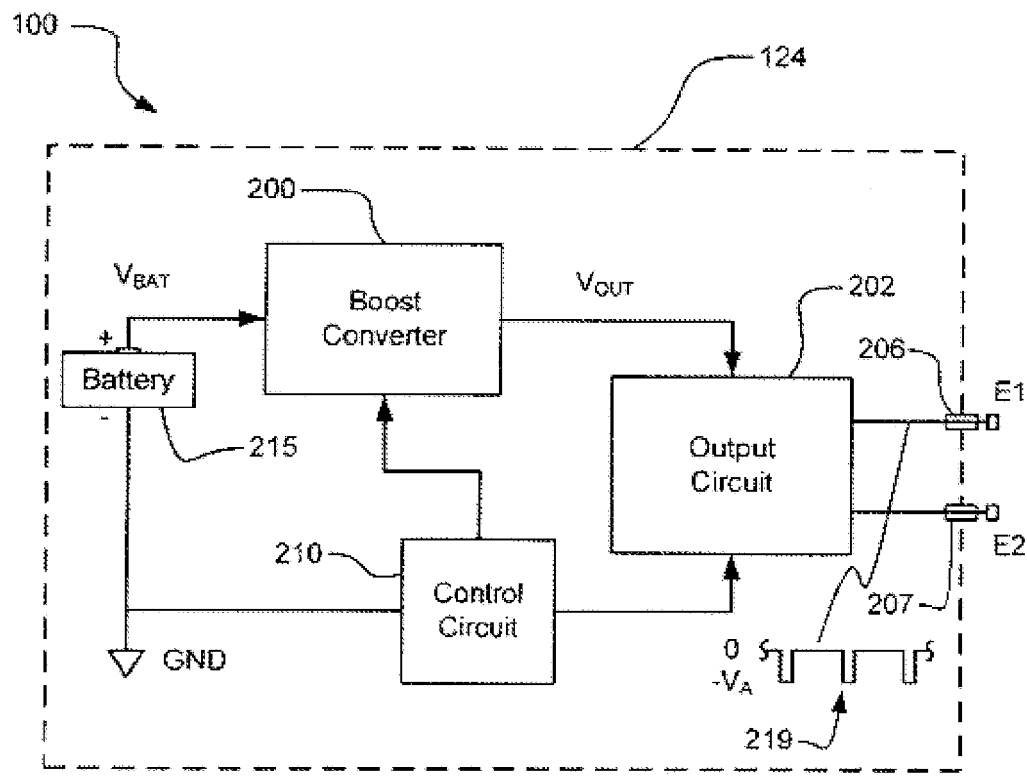
FIG. 8 illustrates a functional block diagram of the electronic circuits used within an IEAD of the type described herein.

FIG. 8 shows a functional block diagram of an implantable electroacupuncture device (IEAD) 100 made in accordance with the teachings disclosed herein. As seen in FIG. 8, the IEAD 100 uses an implantable battery 215 having a battery voltage VBAT. In one preferred embodiment, this battery 215 comprises a lithium battery having a nominal output voltage of 3 V, such as the CR1612 battery manufactured by Panasonic. Also included within the IEAD 100 is a Boost Converter circuit 200, an Output Circuit 202 and a Control Circuit 210. The battery 115, boost converter circuit 200, output circuit 202 and control circuit 210 are all housed within an hermetically sealed housing 124.

As controlled by the control circuit 210, the output circuit 202 of the IEAD 100 generates a sequence of stimulation pulses that are delivered to electrodes E1 and E2, through feed-through terminals 206 and 207, respectively, in accordance with a prescribed stimulation regimen. A coupling capacitor CC is also employed in series with at least one of the feed-through terminals 206 or 207 to prevent DC (direct current) current from flowing into the patient's body tissue.

Figure 12:
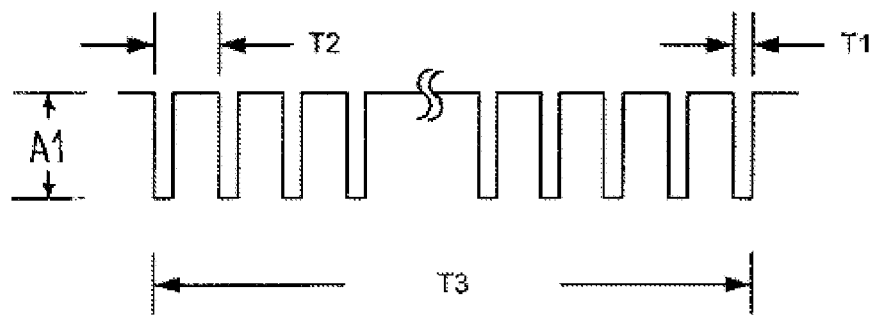
FIGS. 12 and 13 show timing waveform diagrams that illustrate the stimulus signal generated by the IEAD and the parameters associated with such stimulus signal that may be adjusted or programmed to define the stimulation regimen.

As explained more fully below in connection with the description of the timing waveform diagrams presented in FIGS. 12 and 13, the prescribed stimulation regimen typically comprises a continuous stream of stimulation pulses having a fixed amplitude, e.g., A1 volts, a fixed pulse width, e.g., 0.5 millisecond, and at a fixed frequency, e.g., 2 Hz, during each stimulation session. The stimulation session, also as part of the stimulation regimen, is generated at a very low duty cycle, e.g., for 30 minutes once each week. Other stimulation regimens may also be used, e.g., using a variable frequency for the stimulus pulse during a stimulation session rather than a fixed frequency. Also, the rate of occurrence of the stimulation session may be varied from as short as, e.g., 1 day, to as long as, e.g., 14 days.

In one preferred embodiment, the electrodes E1 and E2 form an integral part of the housing 124. That is, electrode E2 may comprise a circumferential anode electrode that surrounds a cathode electrode E1. The cathode electrode E1, for the embodiment described here, is electrically connected to the case 124 (thereby making the feed-through terminal 206 unnecessary).

In a second preferred embodiment, particularly well-suited for implantable electrical stimulation devices, the anode electrode E2 is electrically connected to the case 124 (thereby making the feed-through terminal 207 unnecessary). The cathode electrode E1 is electrically connected to the circumferential electrode that surrounds the anode electrode E2. That is, the stimulation pulses delivered to the target tissue location (i.e., to the selected acupoint) through the electrodes E1 and E2 are, relative to a zero volt ground (GND) reference, negative stimulation pulses, as shown in the waveform diagram near the lower right hand corner of FIG. 8. (Note, the waveform diagram included in the lower right hand corner of FIG. 8 shows the amplitude to be $-V_A$ volts. The timing waveform diagram shown in FIG. 12 shows the amplitude to be "A1". A1 and $V_A$ are thus equivalent nomenclature mechanisms for depicting the amplitude of a waveform signal. This amplitude could be expressed in either units of voltage or current.)

Thus, in the embodiment described in FIG. 8, it is seen that during a stimulation pulse the electrode E2 functions as an anode, or positive (+) electrode, and the electrode E1 functions as a cathode, or negative (−) electrode.

The battery 115 provides all of the operating power needed by the EA device 100. The battery voltage $V_{BAT}$ is not the optimum voltage needed by the circuits of the EA device, including the output circuitry, in order to efficiently generate stimulation pulses of amplitude, e.g., $-V_A$ volts. The amplitude $V_A$ of the stimulation pulses is typically many times greater than the battery voltage $V_{BAT}$. This means that the battery voltage must be "boosted", or increased, in order for stimulation pulses of amplitude $V_A$ to be generated. Such "boosting" is done using the boost converter circuit 200. That is, it is the function of the Boost Converter circuit 200 to take its input voltage, $V_{BAT}$, and convert it to another voltage, e.g., $V_{OUT}$, which voltage $V_{OUT}$ is needed by the output circuit 202 in order for the IEAD 100 to perform its intended function.

The IEAD 100 shown in FIG. 8, and packaged as described above in connection with FIGS. 1-7, advantageously provides a tiny self-contained, coin-sized stimulator that may be implanted in a patient at or near a specified acupoint in order to favorably treat a condition or disease of a patient. The coin-sized stimulator advantageously applies electrical stimulation pulses at very low levels and low duty cycles in accordance with specified stimulation regimens through electrodes that form an integral part of the housing of the stimulator. A tiny coin-cell type battery inside of the coin-sized stimulator provides enough energy for the stimulator to carry out its specified stimulation regimen over a period of several years, despite the fact that the battery typically has a relatively high battery impedance, e.g., greater than 5 ohms, and often as high as 150 ohms, or more. Thus, the coin-sized stimulator, once implanted, provides an unobtrusive, needleless, longlasting, safe, elegant and effective mechanism for treating certain conditions and diseases that have long been treated by acupuncture or electroacupuncture.

Figure 9:
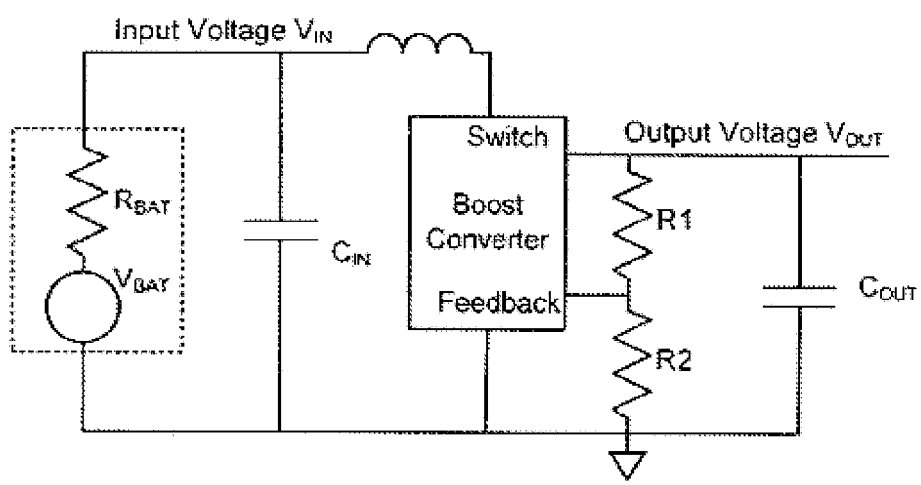
FIG. 9 functionally shows a basic boost converter circuit configuration, and is used to model how the impedance of the battery $R_{BAT}$ can affect its performance.

A boost converter integrated circuit (IC) typically draws current from its power source in a manner that is proportional to the difference between the actual output voltage $V_{OUT}$ and a set point output voltage, or feedback signal. A representative boost converter circuit that operates in this manner is shown in FIG. 9. At boost converter start up, when the actual output voltage is low compared to the set point output voltage, the current drawn from the power source can be quite large. Unfortunately, when batteries are used as power sources, they have internal voltage losses (caused by the battery's internal impedance) that are proportional to the current drawn from them. This can result in under voltage conditions when there is a large current demand from the boost converter at start up or at high instantaneous output current. Current surges and the associated under voltage conditions can lead to undesired behavior and reduced operating life of an implanted electroacupuncture device.

In the boost converter circuit example shown in FIG. 9, the battery is modeled as a voltage source with a simple series resistance. With reference to the circuit shown in FIG. 9, when the series resistance $R_{BAT}$ is small (5 Ohms or less), the boost converter input voltage $V_{IN}$, output voltage $V_{OUT}$ and current drawn from the battery, $I_{BAT}$, typically look like the waveform shown in FIG. 9A, where the horizontal axis is time, and the vertical axis on the left is voltage, and the vertical axis of the right is current.

Figure 9A:
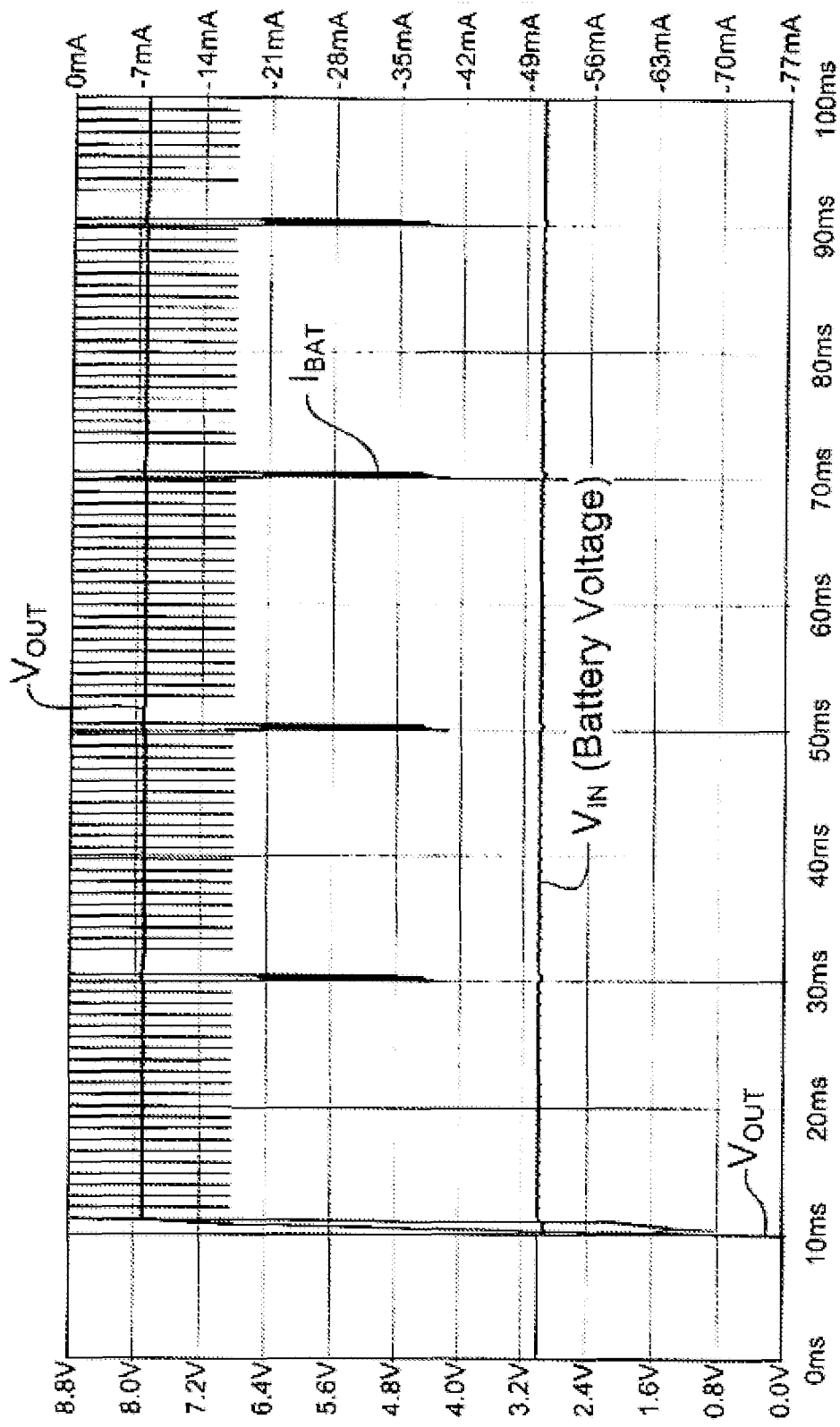
FIG. 9A illustrates a typical voltage and current waveform for the circuit of FIG. 9 when the battery impedance $R_{BAT}$ is small.

Referring to the waveform in FIG. 9A, at boost converter startup (10 ms), there is 70 mA of current drawn from the battery with only ~70 mV of drop in the input voltage $V_{IN}$. Similarly, the instantaneous output current demand for electro-acupuncture pulses draws up to 40 mA from the battery with an input voltage drop of ~40 mV.

Figure 9B:
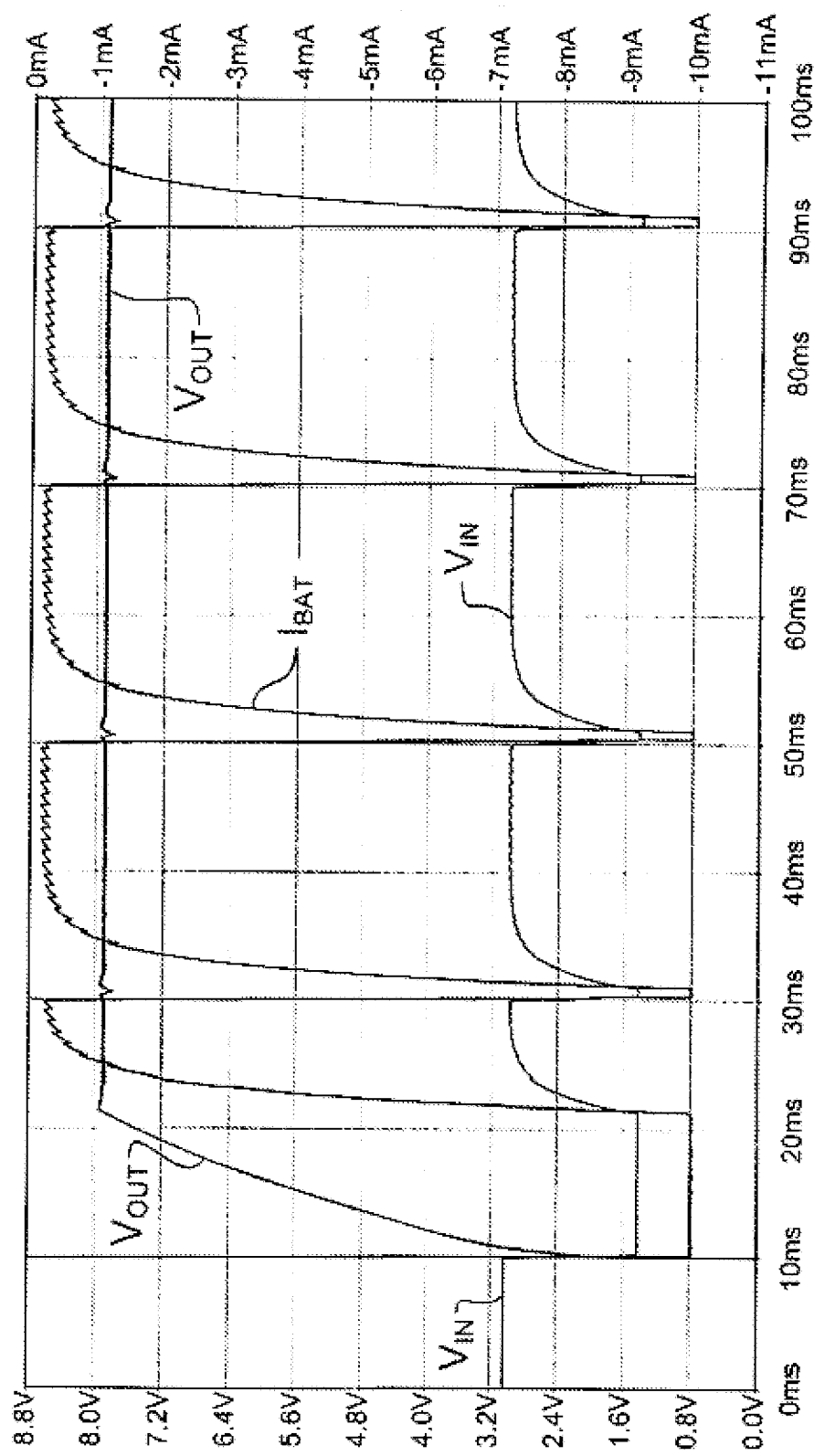
FIG. 9B shows the voltage and current waveform for the circuit of FIG. 9 when the battery impedance $R_{BAT}$ is large.

Disadvantageously, however, a battery with higher internal impedance (e.g., 160 Ohms), cannot source more than a milliampere or so of current without a significant drop in output voltage. This problem is depicted in the timing waveform diagram shown in FIG. 9B. In FIG. 9B, as in FIG. 9A, the horizontal axis is time, the left vertical axis is voltage, and the right vertical axis is current.

As seen in FIG. 9B, as a result of the higher internal battery impedance, the voltage at the battery terminal ($V_{IN}$) is pulled down from 2.9 V to the minimum input voltage of the boost converter (~1.5 V) during startup and during the instantaneous output current load associated with electro-acupuncture stimulus pulses. The resulting drops in output voltage $V_{OUT}$ are not acceptable in any type of circuit except an uncontrolled oscillator circuit.

Also, it should be noted that although the battery used in the boost converter circuit is modeled in FIG. 8B as a simple series resistor, battery impedance can arise from the internal design, battery electrode surface area and different types of electrochemical reactions. All of these contributors to battery impedance can cause the voltage of the battery at the battery terminals to decrease as the current drawn from the battery increases.

In a suitably small and thin implantable electroacupuncture device (IEAD) of the type disclosed herein, it is desired to use a higher impedance battery in order to assure a small and thin device, keep costs low, and/or to have low self-discharge rates. The battery internal impedance also typically increases as the battery discharges. This can limit the service life of the device even if a new battery has acceptably low internal impedance. Thus, it is seen that for the IEAD 100 disclosed herein to reliably perform its intended function over a long period of time, a circuit design is needed for the boost converter circuit that can manage the instantaneous current drawn from $V_{IN}$ of the battery. Such current management is needed to prevent the battery's internal impedance from causing VIN to drop to unacceptably low levels as the boost converter circuit pumps up the output voltage $V_{OUT}$ and when there is high instantaneous output current demand, as occurs when stimulation pulses are generated.

Figure 10:
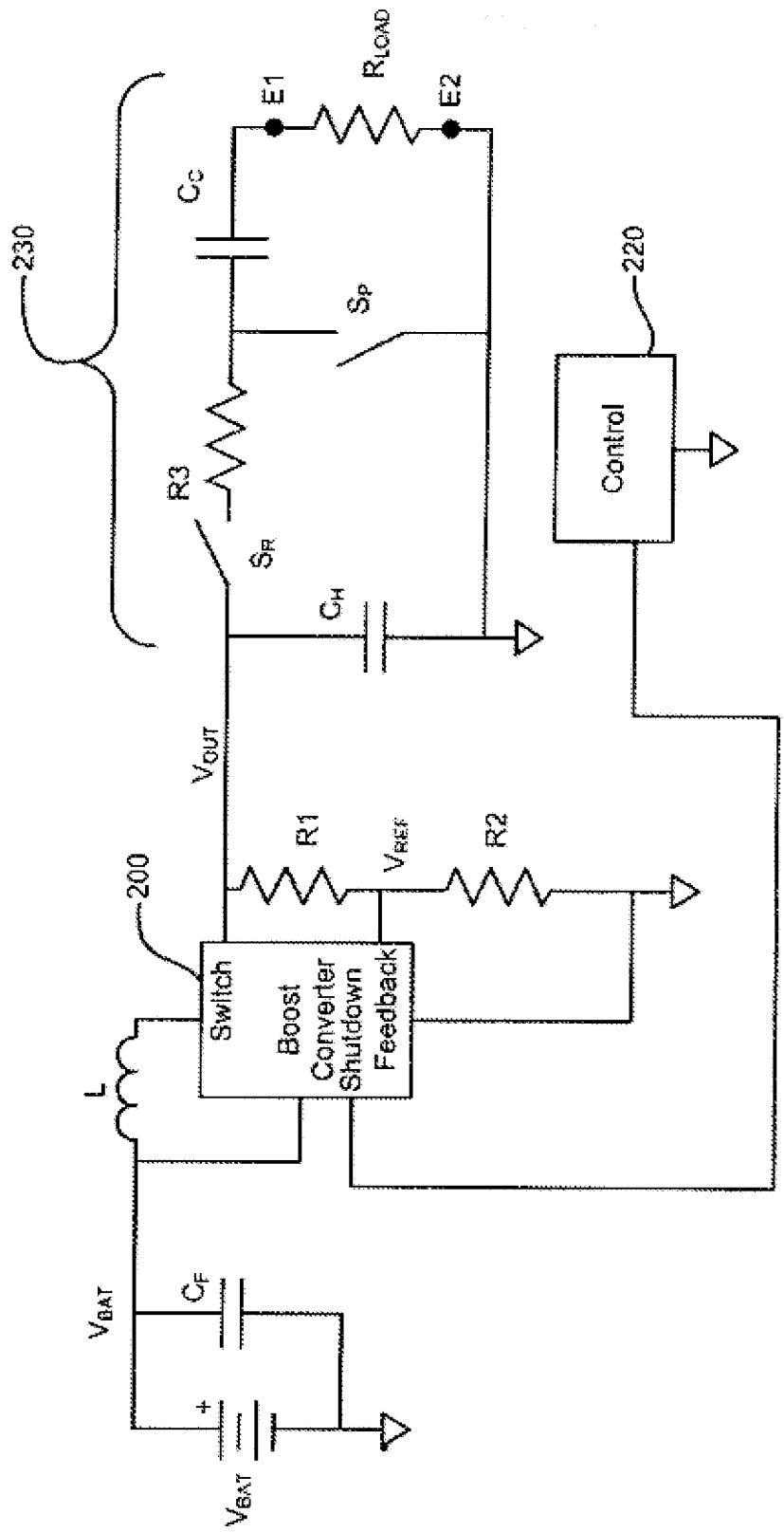
FIG. 10 shows one preferred boost converter circuit and a functional pulse generation circuit configuration for use within the IEAD.

To provide this needed current management, the IEAD 100 disclosed herein employs electronic circuitry as shown in FIG. 10, or equivalents thereof. Similar to what is shown in FIG. 9, the circuitry of FIG. 10 includes a battery, a boost converter circuit 200, an output circuit 230, and a control circuit 220. The control circuit 220 generates a digital control signal that is used to duty cycle the boost converter circuit 200ON and OFF in order to limit the instantaneous current drawn from the battery. That is, the digital control signal pulses the boost converter ON for a short time, but then shuts the boost converter down before a significant current can be drawn from the battery. In conjunction with such pulsing, an input capacitance CF is used to reduce the ripple in the input voltage $V_{IN}$. The capacitor $C_F$ supplies the high instantaneous current for the short time that the boost converter is ON and then recharges more slowly from the battery during the interval that the boost converter is OFF.

A variation of the above-described use of a digital control signal to duty cycle the boost converter circuit 200 ON and OFF is to let the digital control be generated within the boost converter 200 itself (without having to use a separate control circuit 220). In accordance with this variation, the boost converter circuit 200 shuts itself down whenever the battery voltage falls below a predetermined level above that required by the remaining circuitry. For example, the MAX8570 boost converter IC, commercially available from Maxim, shuts down when the applied voltage falls below 2.5 V. This is still a high enough voltage to ensure the microprocessor and other circuitry remain operational. Thus, as soon as the input voltage drops below 2.5 volts, the boost converter circuit shuts down, thereby limiting the instantaneous current drawn from the battery. When the boost converter shuts down, the instantaneous battery current drawn from the battery is immediately reduced a significant amount, thereby causing the input voltage to increase. The boost converter remains shut down until the microprocessor (e.g., the circuit U2 shown in FIG. 13A, described below), and/or other circuitry used with the boost converter, determine that it is time to turn the boost converter back ON. Once turned ON, the boost converter remains ON until, again, the input voltage drops to below 2.5 volts. This pattern continues, with the boost converter being ON for a short time, and OFF for a much longer time, thereby controlling and limiting the amount of current that can be drawn from the battery.

In the circuitry shown in FIG. 10, it is noted that the output voltage $V_{OUT}$ generated by the boost converter circuit 200 is set by the reference voltage $V_{REF}$ applied to the set point or feedback terminal of the boost converter circuit 200. For the configuration shown in FIG. 10, $V_{REF}$ is proportional to the output voltage $V_{OUT}$, as determined by the resistor dividing network of R1 and R2.

The switches $S_P$ and $S_R$, shown in FIG. 10 as part of the output circuit 230, are also controlled by the control circuit 220. These switches are selectively closed and opened to form the EA stimulation pulses applied to the load, $R_{LOAD}$. Before a stimulus pulse occurs, switch $S_R$ is closed sufficiently long for the circuit side of coupling capacitor $C_C$ to be charged to the output voltage, $V_{OUT}$. The tissue side of $C_C$ is maintained at 0 volts by the cathode electrode E2, which is maintained at ground reference. Then, for most of the time between stimulation pulses, both switches $S_R$ and $S_P$ are kept open, with a voltage approximately equal to the output voltage $V_{OUT}$ appearing across the coupling capacitor $C_C$.

At the leading edge of a stimulus pulse, the switch $S_P$ is closed, which immediately causes a negative voltage $-V_{OUT}$ to appear across the load, $R_{LOAD}$, causing the voltage at the anode E1 to also drop to approximately $-V_{OUT}$, thereby creating the leading edge of the stimulus pulse. This voltage starts to decay back to 0 volts as controlled by an RC (resistor-capacitance) time constant that is long compared with the desired pulse width. At the trailing edge of the pulse, before the voltage at the anode E1 has decayed very much, the switch $S_P$ is open and the switch $S_R$ is closed. This action causes the voltage at the anode E1 to immediately (relatively speaking) return to 0 volts, thereby defining the trailing edge of the pulse. With the switch $S_R$ closed, the charge on the circuit side of the coupling capacitor $C_C$ is allowed to charge back to $V_{OUT}$ within a time period controlled by a time constant set by the values of capacitor $C_C$ and resistor R3. When the circuit side of the coupling capacitor $C_C$ has been charged back to $V_{OUT}$, then switch $S_R$ is opened, and both switches $S_R$ and $S_P$ remain open until the next stimulus pulse is to be generated. Then the process repeats each time a stimulus pulse is to be applied across the load.

Thus, it is seen that in one embodiment of the electronic circuitry used within the IEAD 100, as shown in FIG. 10, a boost converter circuit 200 is employed which can be shut down with a control signal. The control signal is ideally a digital control signal generated by a control circuit 220 (which may be realized using a microprocessor or equivalent circuit). The control signal is applied to the low side (ground side) of the boost converter circuit 200 (identified as the "shutdown" terminal in FIG. 10). A capacitor $C_F$ supplies instantaneous current for the short ON time that the control signal enables the boost converter circuit to operate. And, the capacitor $C_F$ is recharged from the battery during the relatively long OFF time when the control signal disables the boost converter circuit.

It is also seen that in a variation of the embodiment shown in FIG. 10, a boost converter circuit 200 is used that shuts itself down whenever the input voltage falls below a prescribed threshold, e.g., 2.5 V. The boost converter remains shut down until other circuitry used with the boost converter determines that it is time to turn the boost converter back ON, e.g., whenever the feedback signal indicates the output voltage $V_{OUT}$ has fallen below a prescribed threshold, and/or whenever a prescribed period of time has elapsed since the last stimulus pulse was generated.

Figure 11:
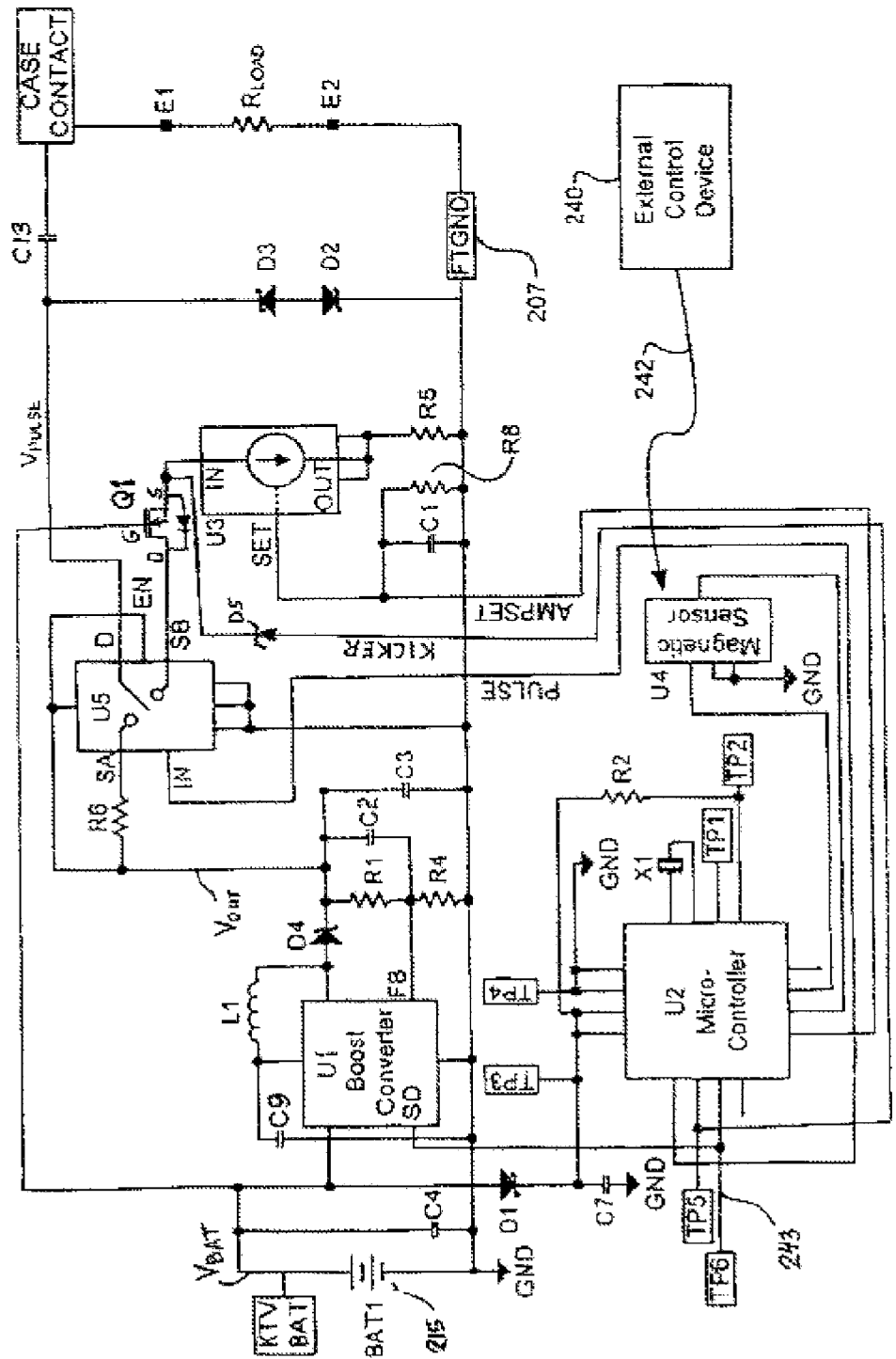
FIG. 11 depicts one preferred schematic configuration for an IEAD that utilizes a boost converter circuit U1, micro-controller circuit U2, programmable current source U3, sensor U4 and switch circuit U5 in order to perform the functions illustrated in the functional diagrams of FIGS. 7, 18, 19 and 20.

One preferred circuit implementation of the embodiment of the circuitry shown in FIG. 10 is shown in the schematic diagram presented in FIG. 11. That is, the circuitry depicted in the schematic diagram of FIG. 11 performs all of the functions illustrated in connection with the functional circuitry illustrated in FIG. 10. Additionally, the circuitry shown In FIG. 11 provides a few other additional features not necessarily evident from the functional diagram of FIG. 10, but which features nonetheless contribute to the overall utility and functionality of the IEAD circuitry shown in FIG. 11.

There are five integrated circuits (ICs) used as the main components of the IEAD circuitry shown in FIG. 11. The IC U1 is a boost converter circuit, and performs the function of the boost converter circuit 200 described previously in connection with FIGS. 8 and 9.

Still referring to FIG. 11, the IC U2 is a micro-controller IC and is used to perform the function of the control circuit 210 described previously in connection with FIG. 8, or the control circuit 220 described previously in connection with FIG. 10. A preferred IC for this purpose is a MSP430G2452 micro-controller chip made by Texas Instruments. This chip includes 8 KB of Flash memory. Having some memory included with the micro-controller is important because it allows the parameters associated with a selected stimulation regimen to be defined and stored. One of the advantages of the IEAD described herein is that it provides a stimulation regimen that can be defined with just 5 parameters, which five parameters are clearly evident from the timing waveform diagrams of FIGS. 12 and 13, and their accompanying descriptions. This allows the programming features of the micro-controller to be carried out in a simple and straightforward manner.

The micro-controller U2 primarily performs the function of generating the digital signal (when used) that shuts down the boost converter circuit to prevent too much instantaneous current from being drawn from the battery $V_{BAT}$, or performs other functions related to controlling and managing the power consumed within the IEAD 100. The micro-controller U2 also controls the generation of the stimulus pulses at the desired pulse width and frequency. It further keeps track of the time periods associated with a stimulation session, i.e., when a stimulation session begins and when it ends.

The micro-controller U2 additionally controls the amplitude of the stimulus pulse. This is done by adjusting the value of a current generated by a Programmable Current Source U3. In one embodiment, U3 is realized with a voltage controlled current source IC. In such a voltage controlled current source, the programmed current is set by a programmed voltage appearing across a fixed resistor R5, i.e., the voltage appearing at the "OUT" terminal of U3. This programmed voltage, in turn, is set by the voltage applied to the "SET" terminal of U3. That is, the programmed current source U3 sets the voltage at the "OUT" terminal to be equal to the voltage applied to the "SET" terminal. The programmed current that flows through the resistor R5 is then set by Ohms Law to be the voltage at the "set" terminal divided by R5. As the voltage at the "set" terminal changes, the current flowing through resistor R5 at the "OUT" terminal changes, and this current is essentially the same as the current flowing through the load $R_{LOAD}$. Hence, whatever current flows through resistor R5, as set by the voltage across resistor R5, is essentially the same current that flows through the load $R_{LOAD}$. Thus, as the micro-controller U2 sets the voltage at the "set" terminal of U3, on the signal line labeled "AMPSET", it controls what current flows through the load $R_{LOAD}$. In no event can the amplitude of the voltage pulse developed across the load $R_{LOAD}$ exceed the voltage $V_{OUT}$ developed by the boost converter less the voltage drop across the switch U5 and current source U3.

It is important that the circuitry used in the IEAD 100, e.g., the circuitry shown in FIG. 10 or 11, or equivalents thereof, have some means for controlling the stimulation current that flows through the load, $R_{LOAD}$, which load may be characterized as the patient's tissue impedance at and around the acupoint or other target location that is being stimulated. This tissue impedance may typically vary from between about 300 ohms to 2000 ohms. Moreover, it not only varies from one patient to another, but it varies over time for the same patient. Hence, there is a need to control the current that flows through this variable load, $R_{LOAD}$. One way of accomplishing this goal is to control the stimulation current, as opposed to the stimulation voltage, so that the same current will flow through the tissue load regardless of changes that may occur in the tissue impedance over time. The use of a voltage controlled current source U3, as shown in FIG. 11, is one way to satisfy this need.

Still referring to FIG. 11, a fourth IC U4 is connected to the micro-controller U2. For the embodiment shown in FIG. 11, the circuit U4 is an electromagnetic field sensor, and it allows the presence of an externally-generated (non-implanted) electromagnetic field to be sensed. An "electromagnetic" field, for purposes of this application includes magnetic fields, radio frequency (RF) fields, light fields, and the like. The electromagnetic sensor may take many forms, such as any wireless sensing element, e.g., a pickup coil or RF detector, a photon detector, a magnetic field detector, and the like. When a magnetic sensor is employed as the electromagnetic sensor U4, the magnetic field is generated using an External Control Device (ECD) 240 that communicates wirelessly, e.g., through the presence or absence of a magnetic field, with the magnetic sensor U4. (A magnetic field, or other type of field if a magnetic field is not used, is symbolically illustrated in FIG. 11 by the wavy line 242.) In its simplest form, the ECD 240 may simply be a magnet, and modulation of the magnetic field is achieved simply by placing or removing the magnet next to or away from the IEAD. When other types of sensors (non-magnetic) are employed, the ECD 240 generates the appropriate signal or field to be sensed by the sensor that is used.

Use of the ECD 240 provides a way for the patient, or medical personnel, to control the IEAD 100 after it has been implanted (or before it is implanted) with some simple commands, e.g., turn the IEAD ON, turn the IEAD OFF, increase the amplitude of the stimulation pulses by one increment, decrease the amplitude of the stimulation pulses by one increment, and the like. A simple coding scheme may be used to differentiate one command from another. For example, one coding scheme is time-based. That is, a first command is communicated by holding a magnet near the IEAD 100, and hence near the magnetic sensor U4 contained within the IEAD 100, for differing lengths of time. If, for example, a magnet is held over the IEAD for at least 2 seconds, but no more than 7 seconds, a first command is communicated. If a magnet is held over the IEAD for at least 11 seconds, but no more than 18 seconds, a second command is communicated, and so forth. Various other coding schemes that could be employed for this purpose are described in Applicant's Parent Application, referenced above.

More sophisticated magnetic coding schemes may be used to communicate to the micro-controller chip U2 the operating parameters of the IEAD 100. For example, using an electromagnet controlled by a computer, the pulse width, frequency, and amplitude of the EA stimulation pulses used during each stimulation session may be pre-set. Also, the frequency of the stimulation sessions can be pre-set. Additionally, a master reset signal can be sent to the device in order to re-set these parameters to default values. These same operating parameters and commands may be re-sent at any time to the IEAD 100 during its useful lifetime should changes in the parameters be desired or needed.

Additional features associated with the use and operation of the circuitry of FIG. 11 which are not included through operation of the functional circuitry shown in FIG. 10, relate to the inclusion of a Schottky diode D4 at the output terminal LX of the boost convertor circuit U1 and the inclusion of a fifth integrated circuit (IC) U5, which circuit U5 essentially performs the same function as the switches $S_R$ and $S_P$ shown in FIG. 10.

The Schottky diode D4 helps isolate the output voltage $V_{OUT}$ generated by the boost converter circuit U1. This is important in applications where the boost converter circuit U1 is selected and operated to provide an output voltage $V_{OUT}$ that is four or five times as great as the battery voltage, $V_{BAT}$. For example, in the embodiment for which the circuit of FIG. 11 is designed, the output voltage $V_{OUT}$ is designed to be nominally 15 volts (and could be as high as 25 volts) using a battery that has a nominal battery voltage of only 3 volts.

The inclusion of the fifth IC U5 in the circuit shown in FIG. 11 is, as indicated, used to perform the function of a switch. More particularly, the IC U5 shown in FIG. 11 functions as a single pole/double throw (SPDT) switch. Numerous commercially-available ICs may be used for this switch function. For example, an ADG1419 IC, available from Analog Devices Incorporated (ADI) may be used. In such IC U5, the terminal "D" functions as the common terminal of the switch, and the terminals "SA" and "SB" function as the selected output terminal of the switch. The terminals "IN" and "EN" are control terminals to control the position of the switch. Thus, when there is a signal present on the PULSE line, which is connected to the "IN" terminal of U5, the SPDT switch U5 connects the "D" terminal to the "SB" terminal, and the SPDT switch U5 effectively connects the cathode electrode E1 to the programmable current source U3. This connection thus causes the programmed current, set by the control voltage AMPSET applied to the SET terminal of the programmable current source U3, to flow through resistor R5, which in turn causes essentially the same current to flow through the load, $R_{LOAD}$, present between the electrodes E1 and E2. When a signal is not present on the PULSE line, the SPDT switch U5 effectively connects the cathode electrode E1 to the resistor R6, which allows the coupling capacitors C12 and C13 to recharge back to the voltage $V_{OUT}$ provided by the boost converter circuit U2.

The schematic diagram of FIG. 11, which shows the circuit implementation used within the IEAD 100, further includes a boost converter circuit U1 that is modulated ON and OFF using digital control generated within the boost converter circuit U1 itself. In accordance with this implementation, as explained briefly previously, the boost converter circuit 200 shuts itself down whenever the battery voltage falls below a predetermined level above that required by the remaining circuitry. For example, in the embodiment shown in FIG. 11, the boost converter circuit U1 is realized using a MAX8570 boost converter IC, commercially available from Maxim, or equivalents thereof. This particular boost converter IC shuts down when the applied voltage, $V_{BAT}$, falls below 2.5 V. Advantageously, a battery voltage of 2.5 volts is still a high enough voltage to ensure the microcontroller IC U2, and other circuitry associated with the operation of the IEAD 100, remain operational.

Thus, in operation, as soon as the battery voltage drops below 2.5 volts, the boost converter circuit U1 shuts down, thereby limiting the instantaneous current drawn from the battery. When the boost converter U1 shuts down, the instantaneous battery current drawn from the battery is immediately reduced a significant amount, thereby causing the battery voltage $V_{BAT}$ to increase.

As the battery voltage $V_{BAT}$ increases, the boost converter circuit U1 remains shut down until the microcontroller U2 determines that it is time to turn the boost converter back ON. This turn ON typically occurs in one of two ways: (1) just prior to the delivery of the next stimulus pulse, a turn ON signal may be applied to the Shutdown ("SD") terminal, signal line 243, of the boost converter circuit U1; or (2) as soon as the battery voltage, $V_{BAT}$, has increased a sufficient amount, as sensed at the feedback terminal FB of the boost converter circuit U1, the circuits within the boost converter circuit U1 are automatically turned back ON, allowing the output voltage $V_{OUT}$ to build up to a voltage level needed by the switch circuit U5 and the current source circuit U3 to generate an output stimulus pulse of the desired amplitude when the next PULSE signal is applied to the IN terminal of the switch U5 by the microcontroller U2.

Once turned ON, the boost converter remains ON until, again, the input voltage drops below 2.5 volts. This pattern continues, with the boost converter being ON for a short time, and OFF for a much longer time (typically, the duty cycle associated with this ON/OFF operation of the boost converter circuit U1 is no greater than about 0.01), thereby controlling and limiting the amount of current that is drawn from the battery. This ON/OFF action of U1 assures that the battery voltage, $V_{BAT}$, always remains sufficiently high to permit operation of all the critical circuits of the IEAD 100 (principally the circuits of the microcontroller U2), except the boost converter circuit U1.

In a preferred implementation, the microcontroller circuit U2 used in FIG. 11 comprises an MSP430G2452IRSA 16 microcontroller, commercially available from Texas Instruments, or equivalent microcontroller The programmable current source circuit U3 comprises a LT3092 programmable current source commercially available form Linear Technology, or equivalents thereof. The sensor circuit U4 comprises an AS-M15SA-R magnetic sensor, commercially available from Murata, or equivalents thereof. And, the switch circuit U5 comprises an ADG1419BCPZ single pole double throw analog switch commercially available from Analog Devices, or equivalents thereof.

A further feature or enhancement provided by the circuit implementation depicted in FIG. 11 relates to removing, or at least minimizing, some undesirable leading edge transients that are seen in the output stimulus pulses generated by the circuitry of FIG. 11. The solution to remove or mitigate the occurrence of such leading edge transients is to insert an N-MOSFET transistor switch Q1 at the input terminal, IN, of the programmable current source circuit U3. This switch Q1 acts as a "cascode" stage that maintains a more constant voltage across the current source U3 as the output current and/or load resistance changes. Use of this N-MOSFET switch Q1 as depicted in FIG. 11 as a cascode stage advantageously reduces the transient leading edge of the stimulus pulse because the capacitance looking into Q1 is much less than is seen when looking into the current source circuit U3.

Yet an additional feature or enhancement provided by the circuitry of FIG. 11 is to address a delay that is seen when starting up the programmable current source circuit U3 when programmed to provide low pulse amplitudes, (e.g., less than about 3 mA). A typical current stimulus output for the IEAD is on the order of 15-25 mA. When a much smaller amplitude current stimulus is used, e.g., 1.5-3 mA, the control signal that defines this smaller amplitude pulse is significantly less than the one used to define the more typical stimulus amplitudes of 15-25 mA. Such a small control signal lengthens the delay between a trigger point and the leading edge of a stimulus pulse. This problem is addressed through use a Schottky diode D5 connected from an output port on the microcontroller circuit U2 to the input port, IN, of the current source circuit U3. This Schottky diode D5 is realized, for the embodiment shown in FIG. 11, using a BAT54XV2DKR diode, commercially available from Fairchild Semiconductor. This diode D5 is used to warm-up or "kick start" the circuit U3 when the pulse amplitude is low. Use of the diode D5 allows the microcontroller U2 to drive U3 directly at the start of the pulse, over the signal line labeled "KICKER" in FIG. 11, without significantly changing the pulse characteristics.

Use and Operation

With the implantable electroacupuncture device (IEAD) 100 in hand, the IEAD 100 may be used most effectively to treat a specified disease or medical condition of the patent by first pre-setting stimulation parameters that the device will use during a stimulation session. FIGS. 12 and 13 show a timing waveform diagrams illustrating the EA stimulation parameters used by the IEAD to generate EA stimulation pulses. As seen in FIGS. 12 and 13, there are basically five parameters associated with a stimulation session (4 parameters are shown in FIG. 12, and one additional parameter is shown in FIG. 13). The time T1 defines the duration (or pulse width) of a stimulus pulse. The time T2 defines the time between the start of one stimulus pulse and the start of the next stimulus pulse. The time T2 thus defines the period associated with the frequency of the stimulus pulses. The frequency of the stimulation pulses is equal to 1/T2. The ratio of T1/T2 is typically quite low, e.g., less than 0.01. The duration of a stimulation session is dictated or defined by the time period T3. The amplitude of the stimulus pulses is defined by the amplitude A1. This amplitude may be expressed in either voltage or current.

Figure 13:
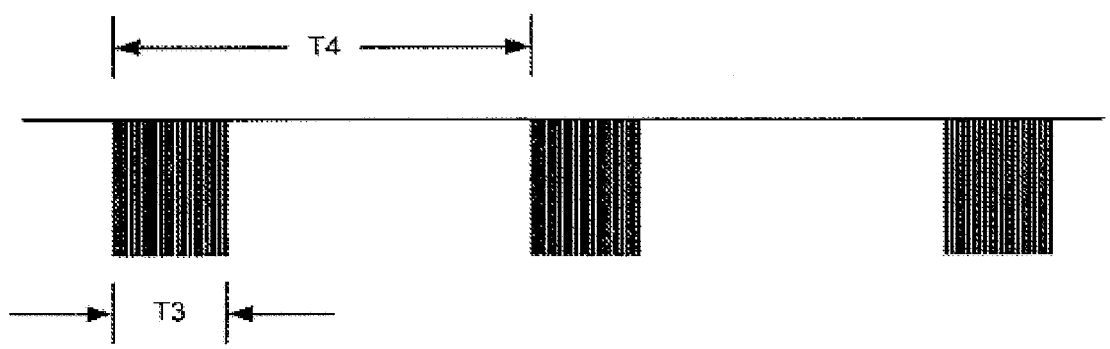

Turning next to FIG. 13, a timing waveform diagram is shown that illustrates the manner in which the stimulation sessions are administered in accordance with a preferred stimulation regimen. FIG. 13 shows several stimulation sessions of duration T3, and how often the stimulation sessions occur. The stimulation regimen thus includes a time period T4 which sets the time period from the start of one stimulation session to the start of the next stimulation session. T4 thus is the period of the stimulation session frequency, and the stimulation session frequency is equal to 1/T4.

In order to allow the applied stimulation to achieve its desired effect on the body tissue at the selected target stimulation site, the period of the stimulation session T4 may be varied when the stimulation sessions are first applied. This can be achieved by employing a simple algorithm within the circuitry of the EA device that changes the value of T4 in an appropriate manner. For example, at start up, the period T4 may be set to a minimum value, T4(min). Then, as time goes on, the value of T4 may be gradually increased until a desired value of T4, T4(final) is reached.

By way of example, if T4(min) is 1 day, and T4(final) is 7 days, the value of T4 may vary as follows once the stimulation sessions begin: T4=1 day for the duration between the first and second stimulation sessions, then 2 days for the duration between the second and third stimulation sessions, then 4 days for the duration between the third and fourth stimulation sessions, and then finally 7 days for the duration between all subsequent stimulation sessions after the fourth stimulation session.

Rather than increasing the value of T4 from a minimum value to a maximum value using a simple doubling algorithm, as described in the previous paragraph, an enhancement is to use a table of session durations and intervals whereby the automatic session interval can be shorter for the first week or so. For example the first 30 minute session could be delivered after 1 day. The second 30 minute session could be delivered after 2 days. The third 30 minute session could be delivered after 4 days. Finally, the fourth 30 minute session could be delivered for all subsequent sessions after 7 days.

If a triggered session is delivered completely, it advances the therapy schedule to the next table entry.

Another enhancement is that the initial set amplitude only takes effect if the subsequent triggered session is completely delivered. If the first session is aborted by a magnet application, the device reverts to a Shelf Mode. In this way, the first session is always a triggered session that occurs in the clinician setting.

Finally, the amplitude and place in the session table are saved in non-volatile memory when they change. This avoids a resetting of the therapy schedule and need to reprogram the amplitude in the event of a device reset.

By way of example, one preferred set of parameters to use to define a stimulation regimen is:
  T1=0.5 milliseconds
  T2=500 milliseconds
  T3=30 minutes
  T4=7 days (10,080 minutes)
  A1=15 volts (across 1 kOhm), or 15 milliamperes (mA)

It is to be emphasized that the values shown above for the stimulation regimen are representative of only one preferred stimulation regimen that could be used.

It is also emphasized that the ranges of values presented in the claims for the parameters used with the invention have been selected after many months of careful research and study, and are not arbitrary. For example, the ratio of T3/T4, which sets the duty cycle, has been carefully selected to be very low, e.g., no more than 0.05. Maintaining a low duty cycle of this magnitude represents a significant change over what others have attempted in the implantable stimulator art. Not only does a very low duty cycle allow the battery itself to be small (coin cell size), which in turn allows the IEAD housing to be very small, which makes the IEAD ideally suited for being used without leads, thereby making it relatively easy to implant the device at the desired stimulation site (e.g., acupoint), but it also limits the frequency and duration of stimulation sessions.

Limiting the frequency and duration of the stimulation sessions is a key aspect of Applicant's invention because it recognizes that some treatments, such as treating overweight conditions, are best done slowly and methodically, over time, rather than quickly and harshly using large doses of stimulation (or other treatments) aimed at forcing a rapid change in the patient's condition. Moreover, applying treatments slowly and methodically is more in keeping with traditional acupuncture methods (which, as indicated previously, are based on over 2500 years of experience). In addition, this slow and methodical conditioning is consistent with the time scale for remodeling of the central nervous system needed to produce a sustained therapeutic effect. Thus, Applicant has based its treatment regimen on the slow-and-methodical approach, as opposed to the immediate-and-forced approach adopted by many, if not most, prior art implantable electrical stimulators.

Once the stimulation regimen has been defined and the parameters associated with it have been pre-set into the memory of the micro-controller circuit U2, the IEAD 100 needs to be implanted. Implantation is usually a simple procedure, and is described above in connection, e.g., with the description of FIGS. 1A and 1B.

Figure 14:
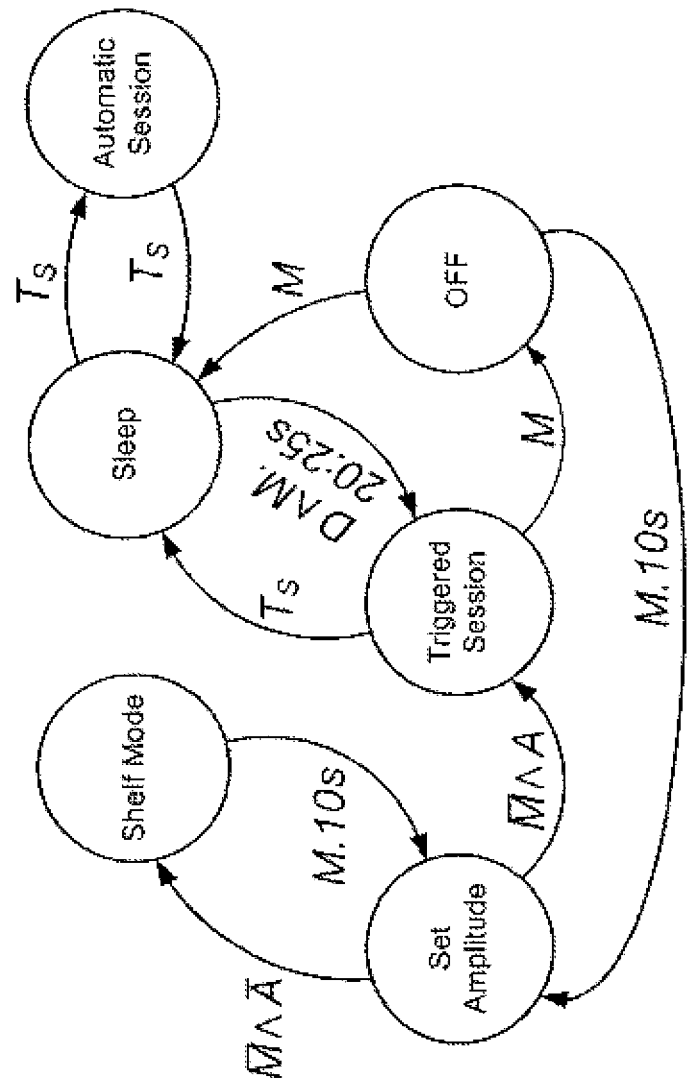
FIG. 14 shows a state diagram that depicts the various states the IEAD may assume as controlled by an external magnet.

After implantation, the IEAD must be turned ON, and otherwise controlled, so that the desired stimulation regimen or stimulation paradigm may be carried out. In one preferred embodiment, control of the IEAD after implantation, as well as anytime after the housing of the IEAD has been hermetically sealed, is performed as shown in the state diagram of FIG. 14. Each circle shown in FIG. 14 represents an operating "state" of the micro-controller U2 (FIG. 11). As seen in FIG. 14, the controller U2 only operates in one of six states: (1) a "Set Amplitude" state, (2) a "Shelf Mode" state, (3) a "Triggered Session" state, (4) a "Sleep" state, (5) an "OFF" state, and an (6) "Automatic Session" state. The "Automatic Session" state is the state that automatically carries out the stimulation regimen using the pre-programmed parameters that define the stimulation regimen.

Shelf Mode is a low power state in which the IEAD is placed prior to shipment. After implant, commands are made through magnet application. Magnet application means an external magnet, typically a small hand-held cylindrical magnet, is placed over the location where the IEAD has been implanted. With a magnet in that location, the magnetic sensor U4 senses the presence of the magnet and notifies the controller U2 of the magnet's presence.

From the "Shelf Mode" state, a magnet application for 10 seconds (M.10s) puts the IEAD in the "Set Amplitude" state. While in the "Set Amplitude" state, the stimulation starts running by generating pulses at zero amplitude, incrementing every five seconds until the patient indicates that a comfortable level has been reached. At that time, the magnet is removed to set the amplitude.

If the magnet is removed and the amplitude is non-zero ($\overline{M} \wedge A$), the device continues into the "Triggered Session" so the patient receives the initial therapy. If the magnet is removed during "Set Amplitude" while the amplitude is zero ($\overline{M} \wedge \overline{A}$), the device returns to the Shelf Mode.

The Triggered Session ends and stimulation stops after the session time (TS) has elapsed and the device enters the "Sleep" state. If a magnet is applied during a Triggered Session (M), the session aborts to the "OFF" state. If the magnet remains held on for 10 seconds (M.10s) while in the "OFF" state, the "Set Amplitude" state is entered with the stimulation level starting from zero amplitude as described.

If the magnet is removed ($\overline{M}$) within 10 seconds while in the OFF state, the device enters the Sleep state. From the Sleep state, the device automatically enters the Automatic Session state when the session interval time has expired (TI). The Automatic Session delivers stimulation for the session time (TS) and the device returns to the Sleep state. In this embodiment, the magnet has no effect once the Automatic Session starts so that the full therapy session is delivered.

While in the Sleep state, if a magnet has not been applied in the last 30 seconds (D) and a magnet is applied for a window between 20-25 seconds and then removed (M.20:25s), a Triggered Session is started. If the magnet window is missed (i.e. magnet removed too soon or too late), the 30 second de-bounce period (D) is started. When de-bounce is active, no magnet must be detected for 30 seconds before a Triggered Session can be initiated.

The session interval timer runs while the device is in Sleep state. The session interval timer is initialized when the device is woken up from Shelf Mode and is reset after each session is completely delivered. Thus abort of a triggered session by magnet application will not reset the timer, the Triggered Session must be completely delivered.

The circuitry that sets the various states shown in FIG. 14 as a function of externally-generated magnetic control commands, or other externally-generated command signals, is the micro-controller U2 (FIG. 11) or the control circuit 220 (FIG. 10). Such processor-type circuits are programmable circuits that operate as directed by a program. The program is often referred to as "code", or a sequence of steps that the processor circuit follows. The "code" can take many forms, and be written in many different languages and formats, known to those of skill in the art. Representative "code" for the micro-controller U2 (FIG. 11) for controlling the states of the IEAD as shown in FIG. 14 is found in Appendix C, attached hereto, and incorporated by reference herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense and are not intended to be exhaustive or to limit the invention to any precise form disclosed. Many modifications and variations are possible in light of the above teaching. Thus, while the invention(s) herein disclosed has been described by means of specific embodiments and applications thereof, numerous modifications and variations could be made thereto by those skilled in the art without departing from the scope of the invention(s) set forth in the claims.

What is claimed is:

1. An hermetically sealed, leadless, package for housing an implantable electroacupuncture device (IEAD), comprising:
   a shallow coin-sized case having a bottom plate of width D2 and a side wall connected to a perimeter edge of the bottom plate, the side wall having a height W2, wherein the ratio of W2 to D2 is about 0.1, and wherein D2 is about 25 mm;
   a radial recess formed at one portion of the side wall, said radial recess in the side wall extending radially inward toward the center of the bottom plate, and having a radial depth of D5 measured from the perimeter edge of the bottom plate, the side wall having an opening therein at or near the point where the radial recess has its maximum depth;
   a feed-through pin; and
   an insulating material through which the feed-through pin passes,
   wherein the insulating material is hermetically bonded to the opening in the bottom of the recess, and the surface of the pin is hermetically bonded to the insulating material, and further wherein a distal end of the feed-through pin extends radially outward for at least a distance D5 to the top of the recess, and wherein a proximal end of the feed-through pin extends radially inward towards the center of the coin-sized case;
   at least two electrodes mounted on an outside surface of the coin-sized case, including: (i) a central plate electrode mounted substantially in the center of an outside surface of the bottom plate of the coin-sized case, (ii) a ring electrode placed around the perimeter edge of the bottom plate so as to make electrical contact with the distal end of the feed-through pin, and (iii) an insulating layer of non-conductive material positioned between the ring electrode and the outside surface of the perimeter edge of the bottom plate, thereby preventing the electrode from making electrical contact with the outside surface of the coin-sized case;
   wherein a feed-through assembly is created when electronic circuitry, comprising pulse generation circuitry powered by a thin coin-cell primary battery, is placed inside of the coin-sized case and connected to the proximal end of the feed-through pin, presenting stimulation pulses in accordance with a specified stimulation regimen at the ring electrode, with an electrical return path through the central plate electrode;
   a cover plate welded to the upper edge of the side wall of the coin-sized case, thereby hermetically sealing the electronic circuitry inside of the case and cover, and
   wherein an hermetically-sealed feed-through connection is established between the electronic circuitry on the inside of the coin-sized case and the central and ring electrodes mounted on the outside surface of the coin-sized case.

2. The hermetically sealed IEAD package of claim 1 further including
   a layer of non-conductive material covering all external surface areas of the coin-sized case and cover plate except the circumscribing electrode and plate electrode.

3. The hermetically sealed IEAD package of claim 2 wherein the insulating material through which the feed-through pin passes comprises a ruby or ceramic insulator.

4. The hermetically sealed IEAD package of claim 3 wherein the feed-through pin, ruby insulator, and the bottom of the recess through which the feed-through pin and ruby or ceramic insulator pass are all hermetically sealed as a unit with gold brazing.

5. The feed-through assembly of claim 2 wherein the case and cover are round.

* * * * *